(12) United States Patent
Cervantes

(10) Patent No.: US 8,942,783 B2
(45) Date of Patent: Jan. 27, 2015

(54) STOCHASTIC RESONANCE AND BROWNIAN MOTION FOR THE REDUCTION OF SUDDEN INFANT DEATH SYNDROME (SIDS)

(75) Inventor: Adan R. Cervantes, Marion, IA (US)

(73) Assignee: Element 1 Systems LLC, Marion, IA (US)

(*) Notice: Subject to any disclaimer, the term of this patent is extended or adjusted under 35 U.S.C. 154(b) by 0 days.

(21) Appl. No.: 13/489,030

(22) Filed: Jun. 5, 2012

(65) Prior Publication Data
US 2013/0144152 A1 Jun. 6, 2013

Related U.S. Application Data

(60) Provisional application No. 61/495,223, filed on Jun. 9, 2011.

(51) Int. Cl.
| | |
|---|---|
| *A61B 5/05* | (2006.01) |
| *A61M 21/00* | (2006.01) |
| *A61M 21/02* | (2006.01) |
| *A61B 5/00* | (2006.01) |
| *A61B 8/08* | (2006.01) |
| *A61B 8/02* | (2006.01) |
| *A61B 5/01* | (2006.01) |
| *A61B 5/055* | (2006.01) |
| *A61B 5/145* | (2006.01) |
| *A61B 8/00* | (2006.01) |

(52) U.S. Cl.
CPC ............. *A61M 21/02* (2013.01); *A61B 5/0013* (2013.01); *A61B 8/488* (2013.01); *A61B 8/02* (2013.01); *A61B 5/015* (2013.01); *A61B 5/4812* (2013.01); *A61B 5/055* (2013.01); *A61B 8/0866* (2013.01); *A61B 5/14546* (2013.01); *A61M 21/00* (2013.01); *A61B 8/565* (2013.01); *A61M 2021/0022* (2013.01); *A61M 2021/0027* (2013.01); *A61M 2205/3375* (2013.01); *A61M 2205/3553* (2013.01); *A61M 2205/3584* (2013.01); *A61M 2205/505* (2013.01); *A61M 2205/584* (2013.01); *A61M 2230/06* (2013.01); *A61M 2230/43* (2013.01); *A61M 2230/50* (2013.01)
USPC ................................ 600/407; 600/27; 600/28

(58) Field of Classification Search
USPC ................ 600/407, 409, 27, 28, 534; 606/32; 607/42
See application file for complete search history.

(56) References Cited

U.S. PATENT DOCUMENTS

| | | | | |
|---|---|---|---|---|
| 6,995,558 B2 * | 2/2006 | Butters et al. | ................. | 324/244 |
| 7,477,053 B2 * | 1/2009 | Pinsky et al. | ................. | 324/261 |

OTHER PUBLICATIONS

Hanggi, "Stochastic Resonance in Biology, How Noise Can Enhance Detection of Weak Signals and Help Improve Biological Information Processing", Chemphyschem, 2002, vol. 3, pp. 285-290.*

*Primary Examiner* — Katherine Fernandez
(74) *Attorney, Agent, or Firm* — Schwegman Lundberg & Woessner, P.A.

(57) ABSTRACT

Inventive embodiments include a system for preventing Sudden Infant Death Syndrome (SIDS) in an infant, by the application of Stochastic Resonance neurological stimuli. The system includes a crib mattress and copper noise grids, wherein the copper noise grids are embedded in the crib mattress. The system also includes a mechanism for generating time controlled white noise and time controlled cyclic signals, combined with a multitude of varying frequencies and harmonics, wherein the mechanism is adjustable for measured local (near crib) white noise power density levels, the mechanism further adjustable for diurnal and seasonal white noise power density level changes. The system also includes circuitry effective for producing positive and negative adjustable DC voltage levels.

10 Claims, 27 Drawing Sheets

|  | FEMALE | | MALE | |
|---|---|---|---|---|
| | AWAKE | SLEEP STATES | SLEEP STATES | AWAKE |

| | | | FEMALE | | | MALE | |
|---|---|---|---|---|---|---|---|
| | | AWAKE | SLEEP STATES | | SLEEP STATES | | AWAKE |
| WINTER | DAY | 0 | 5 REM | 7 SWS | 15 SWS | 13 REM | 0 |
| WINTER | NIGHT | 0 | 6 REM | 8 SWS | 16 SWS | 14 REM | 0 |
| SUMMER | DAY | 0 | 1 REM | 2 SWS | 11 SWS | 9 REM | 0 |
| SUMMER | NIGHT | 0 | 3 REM | 4 SWS | 12 SWS | 10 REM | 0 |

| Highest SIDS Risk Kurtosis Scale #16 | Male | Winter | Night | SWS State |
|---|---|---|---|---|
| Lowest SIDS Risk Kurtosis Scale #1 | Female | Summer | Day | REM State |

*FIG. 10B*

| Input from ISSCC | | Crib Frame Corner # 1 | | | Crib Frame Corner # 2 | | | Crib Frame Corner # 3 | | | Crib Frame Corner # 4 | | |
|---|---|---|---|---|---|---|---|---|---|---|---|---|---|
| BCD CLK | Sleep State | A | B | C | A | B | C | A | B | C | A | B | C |
| t = sec | SWS | ON | | | ON | | | ON | | | ON | | |
| t = sec | SWS | | ON | | | ON | | | ON | | | ON | |
| t = sec | SWS | | | ON | | | ON | | | ON | | | ON |
| Awake or REM | | OFF | OFF | OFF | OFF | OFF | OFF | OFF | OFF | OFF | OFF | OFF | OFF |

Brownian Motion Transducer Vibrator Activation Matrix
(From Microcontroller Control 2 Command)

STOCHASTIC RESONANCE AND BROWNIAN MOTION FOR THE REDUCTION OF SUDDEN INFANT DEATH SYNDROME (SIDS)

PRIORITY CLAIM

This patent application claims the benefit of priority of U.S. Provisional Patent Application Ser. No. 61/495,223, entitled STOCHASTIC RESONANCE AND BROWNIAN MOTION FOR THE REDUCTION OF SUDDEN INFANT DEATH SYNDROME (SIDS), which was filed on Jun. 9, 2011, and which is hereby incorporated by reference herein in its entirety.

FIELD

Inventive embodiments disclosed herein related to systems and methods for preventing Sudden Infant Death Syndrome (SIDS).

BACKGROUND OF THE INVENTION

Most studies agree that the cause of SIDS is likely the combination of innate predispositions in the infant and external factors that take advantage of the infant in its most vulnerable developmental stage. Recent medical research points to abnormalities in the serotonin levels of infants who have died from SIDS. While this research holds promising hope in the identification of inherent biological factors in SIDS victims, it does not explain why SIDS deaths occur more prevalently in gender and ethnic groups. Further, there is no discussion to address why more infants die from SIDS in winter months than summer months (northern hemisphere). Clearly, a solution is needed that considers both the innate predispositions to SIDS and the external factors simultaneously.

Presented herein is inventive subject matter which challenges the conventional way of thinking about SIDS. This inventive subject matter considers a multitude of factors, which together form a system that applies external Stochastic Resonance and Brownian Motion neurological stimuli to the infant. Application of Stochastic Resonance and Brownian Motion stimuli affects the voltage-dependent calcium channels and changes the threshold level at which neurotransmitters trigger. The overall result is increased bifurcations on the network of neurons resulting in higher Inter Spike Interval (ISI) frequencies. ISI frequencies increase in oscillation due to the phase following behavior of neurons.

During the Slow Wave Sleep (SWS) state, the infant's respiratory and heart rate are at their lowest and the homeostasis system is most challenged. It is during this sleep state that the infant faces the highest risk of SIDS. System embodiments disclosed herein reduce SIDS by the application of Stochastic Resonance and Brownian Motion as the infant sleeps.

Further, inventive subject matter disclosed herein discloses an explanation for the gender and ethnic disparities of SIDS. In particular, a particle called biogenic magnetite, which interacts with Earth's magnetic field, is known to exist in the human body. Biogenic magnetite aids neuronal excitations near the dendrites, resulting in the activation of more action potentials to fire. Biogenic magnetite is naturally higher in females than in males, which may explain why more male infants than female infants succumb to SIDS. Also, statistically fewer Asian and Caucasian infants die from SIDS than African American, Hispanic or Native American infants, regardless of socioeconomic status. The levels of the biogenic magnetite in the bodies of Asian and Caucasian infants may be higher than in African American, Hispanic, or Native American infants, which may explain the ethnicity gap in SIDS statistics.

The most critical link between the higher incidence of SIDS during winter months (compared to fewer SIDS deaths in the summer) relates to two environmental changes: 1) during winter months, the electromagnetic noise power density is lower than compared to summer months, and 2) Earth's natural resonance frequencies undergo electric and magnetic vector shifts due to the dawn-dusk asymmetry associated with the ionosphere D region layer on the day side of earth, and the disappearance of the D region layer on the night side. Although the electromagnetic noise power difference between a winter night and a summer day is small, it is the change in the phase vectors of the natural resonance frequencies (at the dawn-dusk delimiters) that have the most influence on neuron behavior. Accordingly, inventive subject matter includes a modified crib system which applies neurological stimuli to the infant during sleep. The applied stimuli mimic the natural electromagnetic noise power density that is associated with a typical summer day. The stimuli produces an increase in more neuron action potential to fire and affect the ISI frequencies. The higher oscillating frequencies enhance the autonomous and homeostasis systems and aid the cardiac and respiratory system of the sleeping infant, thus preventing SIDS.

SUMMARY

Inventive embodiments include a system for preventing Sudden Infant Death Syndrome (SIDS) in an infant, by the application of Stochastic Resonance neurological stimuli. The system includes a crib mattress and copper noise grids, wherein the copper noise grids are embedded in the crib mattress. The system also includes a mechanism for generating time controlled white noise and time controlled cyclic signals, combined with a multitude of varying frequencies and harmonics, wherein the mechanism is adjustable for measured local (near crib) white noise power density levels, the mechanism further adjustable for diurnal and seasonal white noise power density level changes. The system also includes circuitry effective for producing positive and negative adjustable DC voltage levels that are time correlated with epochs of infant sleep states and sleep cycles; an application of Brownian Motion Neurological Stimuli, the circuitry having DC voltage levels adjustable as a function of the levels of the infant's measured levels of biogenic ferromagnetic nanoparticles and crystals and adjustable as a function of infant delivery term, infant's Date Of Birth, SIDS probability time line, and SIDS Risk Kurtosis Scale and SIDS Survival Matrix Another inventive embodiment includes a system for preventing Sudden Infant Death Syndrome (SIDS), by the application of Brownian Motion neurological stimulis. The system includes an infant crib motion frame effective for inducing mechanical motion in a multitude of selected directions. The system also includes four or more transducer vibrators effective for inducing small vibrations through the crib motion frame in a multitude of selected directions that are time correlated with epochs of infant sleep states and sleep cycles, and with an application of Stochastic Resonance Neurological Stimuli, wherein the transducer vibrators are adjustable with the Diffusion Coefficient and as a function of the levels of the infant's measured levels of biogenic ferromagnetic nanoparticles and crystals as well as infant delivery term and infant's Date of Birth, SIDS probability time line, SIDS Risk Kurtosis Scale and SIDS Survival Matrix.

One other embodiment includes a system for deriving epochs of infant sleep states and sleep cycles and for producing ON and OFF time commands to Stochastic Resonance and Brownian neurological stimuli circuits. The system includes thermal imaging camera for measuring body temperature changes; Doppler Ultrasound transducer for measuring cardiac and respiratory rate changes; and one or more mechanisms for receiving output from one or more of the thermal imaging camera and Doppler Ultrasound transducer and identifying adaptation of a normal time progression of the ratio of SWS and REM sleep states and cycles, including one or more of SIDS probability time line, SIDS Risk Kurtosis Scale and SIDS Survival Matrix.

One other inventive embodiment includes a method to establish a SIDS Survival Matrix with statistical correlations between levels of biogenic ferromagnetic nanoparticle crystals to incidence of SIDS. The method includes using infant screening with a Superconducting Quantum Interference Device (SQUID) or Magnetic Resonance Imaging (MRI) to detect and measure and logging biogenic magnetite ($FE_3O_4$) and maghemite ($\gamma$-$FE_2O_3$) levels in the infant's body. The method also includes using infant screening with auditory tests with transient evoked otoacoustic emission (TEOAE) hearing screening tests to correlate with levels of biogenic ferromagnetic nanoparticle crystals. The method further includes using neurological stimuli to reduce the incidence of SIDS as a function of the levels of biogenic magnetite ($FE_3O_4$) and maghemite ($\gamma$-$FE_2O_3$) in the infant's body. The method additionally includes using to Stochastic Resonance stimuli with white noise and cyclic signals as neurological stimuli to reduce the incidence of SIDS as a function of the levels biogenic magnetite ($FE_3O_4$) and maghemite ($\gamma$-$FE_2O_3$) and in the infant's body. The method also includes using Brownian Motion Stimuli with a multiple of varying diffusion coefficients as neurological stimuli to reduce the incidence of SIDS as a function of the levels of biogenic magnetite ($FE_3O_4$) and maghemite ($\gamma$-$FE_2O_3$) in the infant's body.

BRIEF DESCRIPTION OF DRAWINGS

FIG. 10B illustrates a view of the SIDS Risk Kurtosis Scale.

DETAILED DESCRIPTION

The following detailed description includes references to embodiments, which are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the inventive subject matter is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Inventive subject matter disclosed herein, a SIDS Reduction Processor (SRP), is designed to provide an infant with a multitude of nonintrusive, touchless and varying stimuli that include 1) neurological stimulation through stochastic noise and, 2) Brownian Motion through very small (millimeter) movement of the crib mattress frame. \

Figure 1:
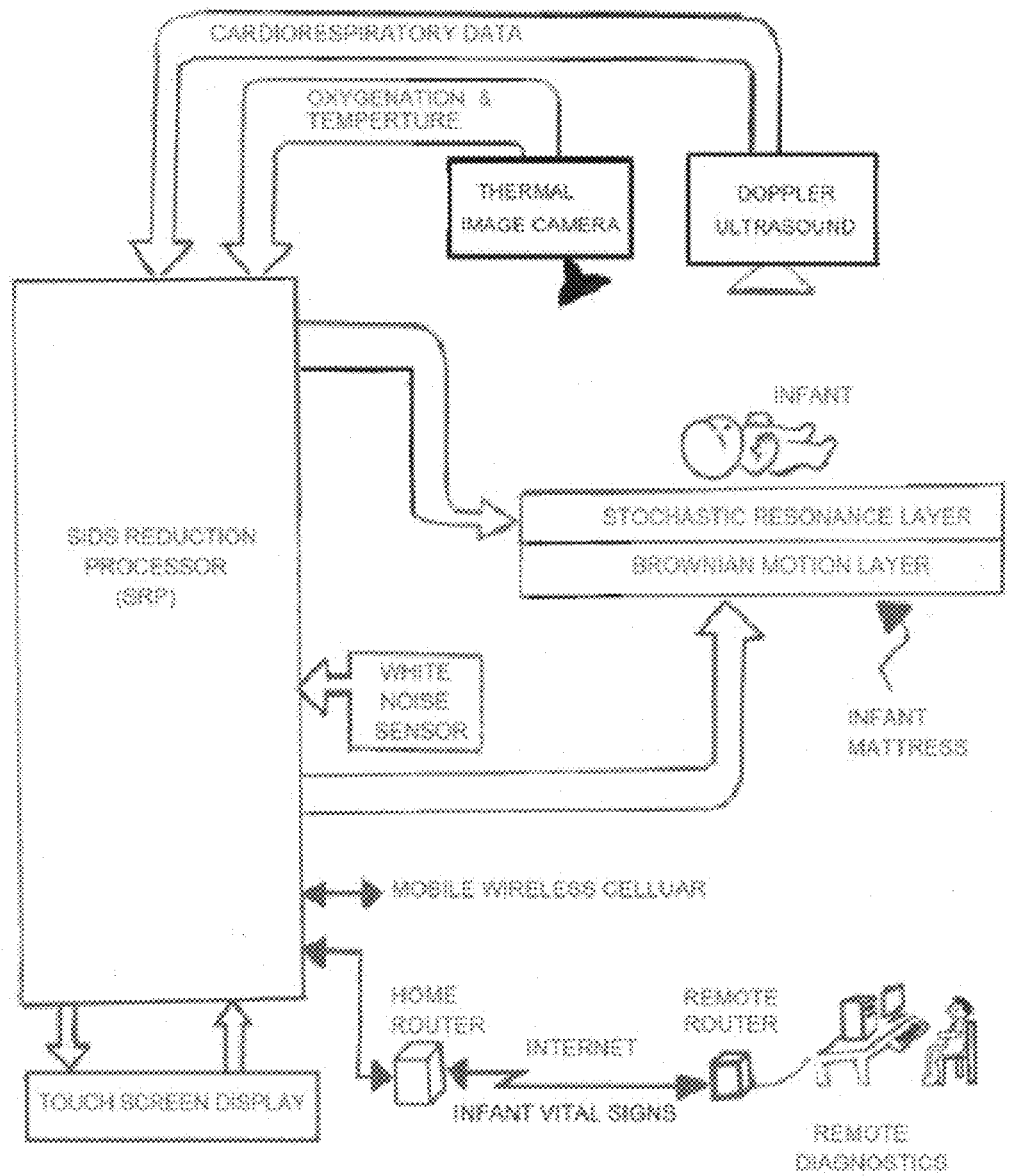
FIG. 1 illustrates one embodiment of a Stochastic Resonance and Brownian Motion, herein SRP, flow diagram of the major components of the SIDS reduction processor (SRP) system.

FIG. 1 illustrates a schematic view of one embodiment of the SRP system. The SRP system embodiment disclosed includes a microcontroller at 10, the SIDS Reduction Processor (SRP) which interfaces with all the subsystems. The SRP system includes a feedback loop, that includes a Doppler Ultrasound transducer 12 and thermal imaging camera 14, which work together to capture data that includes infant temperature, cardiac rate, and respiratory rates. The SRP system embodiment includes a crib mattress 16 with two embedded Stochastic Resonance white noise copper grids 18 and 20 which function to provide neuronal stimuli to an infant 22. For some embodiments, the infant mattress includes a mechanically activated mattress frame 24, shown in FIG. 2 that induces minute (millimeter) Brownian Motion via timed transducer vibrators.

The SRP system embodiment 10 continuously runs a computer program that combines and collects data from the thermal image camera 14 and Doppler Ultrasound transducer 12 to derive epochs of sleep states. Some embodiments of the SRP system interface with Coordinated Universal Time (UTC) servers via the internet to determine date and time of day. This date and time information is coordinated with the infant's date of birth and the current sleep state (REM and SWS) condition to make output intensity level adjustments to the neurological stimuli.

Fine tuning of the neurological stimuli intensity level is made when the gender and ethnicity of the infant is provided to the system. For example, male infants receive slightly higher intensity levels than female infants. Further, after the infant has been tested for biogenic magnetite levels, the results are used to adjust the neurological stimuli to slightly higher intensity levels for infants with lower levels of biogenic magnetite. A touch screen display 26, illustrated in FIG. 2, serves both to input data and output infant state of health data to the display. The SRP system embodiment 10 includes an internet connection 28 to upload infant state of health vitals to a remote secure data base for display to medical professionals or to any web enabled mobile device.

SRP System Operation

Figure 2:
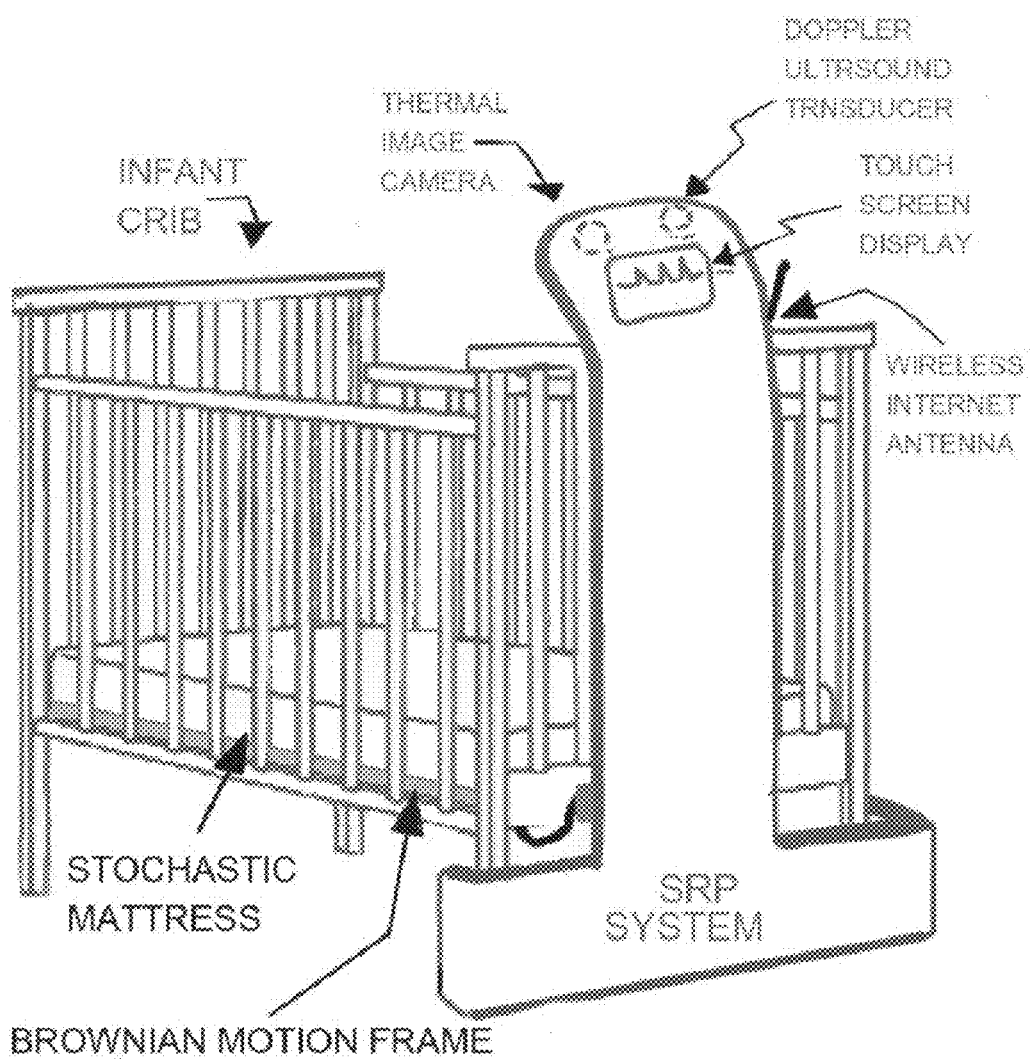
FIG. 2 illustrates a perspective view of one embodiment of the SRP system.

FIG. 2 illustrates one configuration embodiment of the SRP system at 30. The system 30 includes a curved feature over the top of the infant crib slightly with the thermal image camera 14 and Doppler Ultrasound 12 overlooking the infant. A cable 29 connects the SRP microcontroller 10 to the crib mattress 16 to output the Stochastic Resonance white noise stimulus and to output the control data to the Brownian Motion Frame 24.

A white noise sensor 32, illustrated in FIG. 1 is attached to a side of the SRP 10, which measures and collects levels of white noise in the area near the infant crib. A touch screen display 31, illustrated in FIG. 2 is easily accessible and faces toward the parent or care giver. A wireless antenna 28 is attached to the side of the SRP 10 for access to the interne or any mobile web enabled device.

Figure 3:
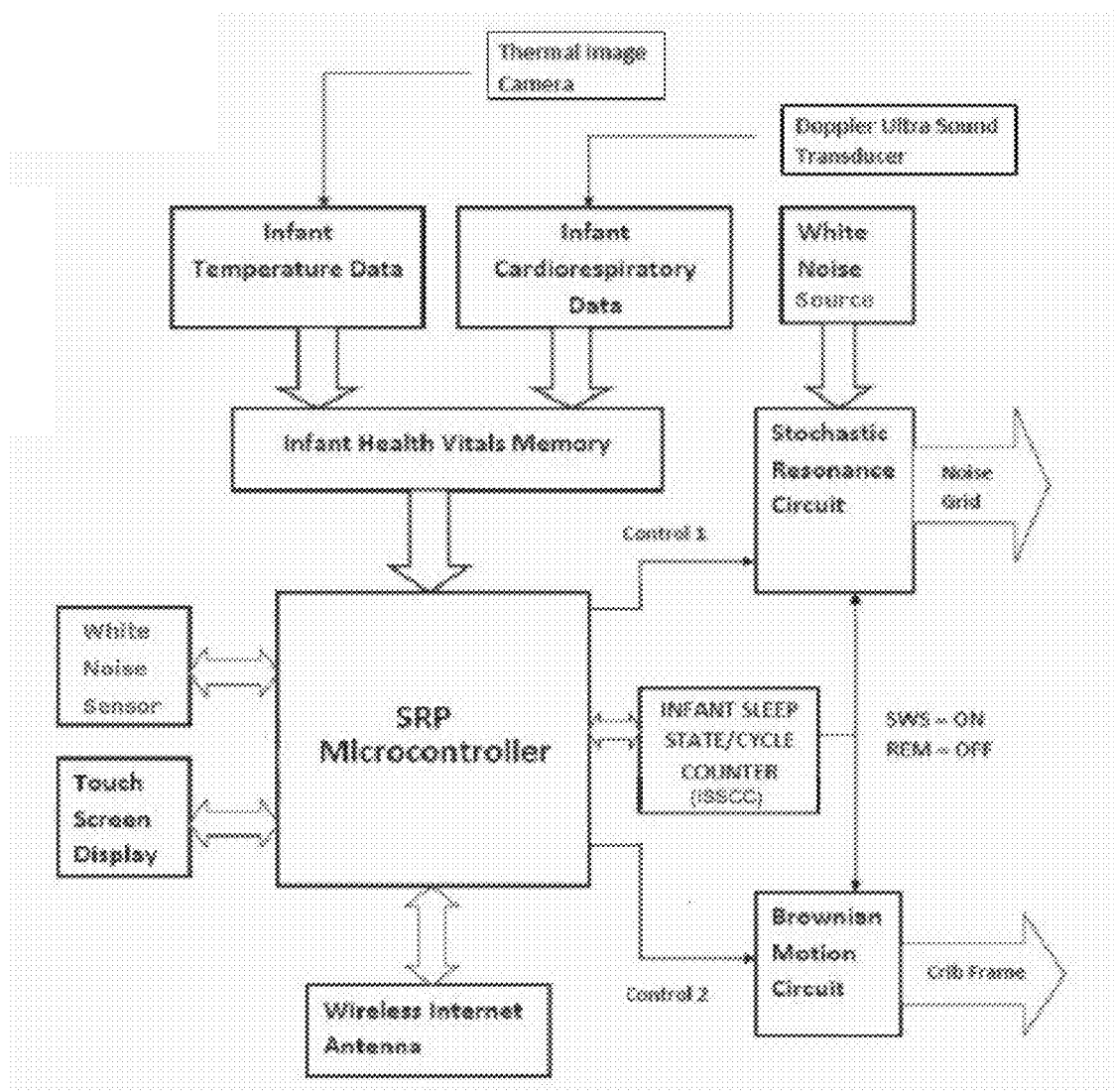
FIG. 3 illustrates one embodiment of an SRP system functional block diagram.

FIG. 3 illustrates at 40 one SRP system functional block diagram. The SRP system incorporates a microcontroller 42 to collect infant health vitals from the Thermal Image camera 42 and Doppler Ultrasound transducer 46.

The SRP system embodiments 10 and 40 determine the infant's sleep states; Slow Wave Sleep (SWS) and Rapid Eye Movement (REM) by measuring changes in the infant's temperature and changes in cardiorespiratory rates. During SWS sleep the temperature of the infant's head decreases slightly and the cardiac and respiratory rates also decrease. During the REM sleep state, the infant's head temperature increase slightly and can be detected as color change by the thermal image camera. The Doppler Ultrasound transducer 46 detects lower cardiac and respiratory rates during the SWS sleep state. The Infant Sleep State/Cycle Counter (ISSCC) records the amount of time that the infant is in the SWS or REM sleep states. At the output of ISSCC 52 is a Control 1 command which goes to the Stochastic Resonance Circuit 54 and the Control 2 command 50 which goes to the Brownian Motion Circuit 56. The ISSCC turns both the Stochastic Resonance Circuit 54 and the Brownian Motion Circuit 56 to the "ON" when the infant is in the SWS sleep state and turns both circuits "OFF" when the infant is in the REM sleep state. A record of the sleep states and sleep cycles is maintained in memory and is later sent to the SRP display and the secure remote website or wireless mobile device.

Mattress Function: Neuronal Stimulus through Stochastic Resonance

Stochastic Resonance as a tool to help reduce the incidence of SIDS was chosen because the SIDS phenomenon manifests itself and fits well with the three basic ingredients of nonlinear systems, which can be characterized by Stochastic Resonance.

A definition of, "Stochastic Resonance" (SR) is found in a paper written by Luca Gammaitoni, Peter Ha"nggi, Peter Jung and Fabio Marchesoni, "Stochastic resonance, Reviews of Modern Physics, vol. 70, no. 1, January 1998, The American Physical Society, pg. 223. The authors defined SR as follows: "The term is given to a phenomenon that is manifest in nonlinear systems whereby generally feeble input information (such as a weak signal) can be amplified and optimized by the assistance of noise. The effect requires three basic ingredients: (i) an energetic activation barrier or, more generally, a form of threshold; (ii) a weak coherent input (such as a periodic signal); (iii) a source of noise that is inherent in the system, or that adds to the coherent input. Given these features, the response of the system undergoes resonance-like behavior as a function of the noise level; hence the name Stochastic Resonance".

The SRP system embodiment disclosed herein is based on these three basic principles of Stochastic Resonance. Specifically, in the context of a SIDS related application, the 1) "form of threshold" is the infant's neuronal network, and 2) "a weak coherent input (such as a periodic signal)" includes cyclic stimuli which are provided to the infant, and 3) "a source of noise that is inherent in the system, or that adds to the coherent input". The SRP system provides these "coherent inputs" to augment the infant's neurological development.

Figure 4:
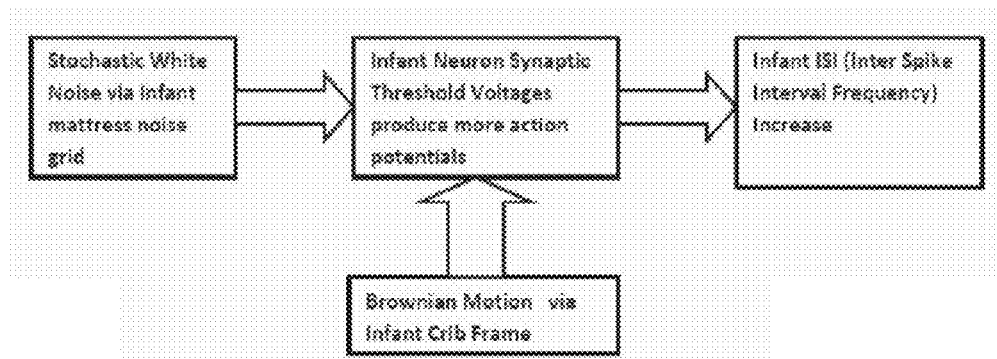
FIG. 4 illustrates a graphical display of Stochastic Resonance/Brownian Motion and neuronal response.

FIG. 4 illustrates one embodiment of Stochastic Resonance/Brownian Motion and neuronal response. SRP system embodiments generate both the Stochastic Noise and Brownian Motion stimuli. During sleep and under the control of the microcontroller, the SRP system embodiments apply neuronal stimulus to the infant via Stochastic Noise and Brownian Motion.

Infant Screening for Biogenic Ferromagnetic Nanoparticles

While the SRP system embodiments disclosed herein have been made to reduce the incidence of SIDS, to optimize performance of the embodiments, it is recommended that a screening test be performed on newborns to determine the levels of ferromagnetic biogenic nanoparticles in the body. Knowing the levels of ferromagnetic biogenic nanoparticles is important because, it is proposed that infants with lower levels of ferromagnetic biogenic nanoparticles may be more neurologically challenged than infants with higher levels of ferromagnetic biogenic nanoparticles.

There are several methods available to measure the levels of ferromagnetic biogenic nanoparticles in the body. Parents can request screening tests of their newborns for ferromagnetic nanoparticles such as magnetite ($FE_3O_4$) and maghemite ($\gamma$-$FE_2O_3$) with a magnetic microscopy instrument such as a Superconducting Quantum Interference Device (SQUID) or Magnetic Resonance Imaging (MRI) test. An alternative is to perform auditory tests with Transient Evoked Otoacoustic Emission (TEOAE) hearing screening tests. The results of these tests are usable to indirectly derive the levels of biogenic magnetite crystals in the fluid of the ear channel, since biogenic magnetite is known to affect the sensitivity of hearing. These tests are usable as a method to assign a higher probability of SIDS to those infants with reduced hearing (this is an assumption;—that the same level of biogenic magnetite exists proportionally throughout the rest of the infant's body). After the number of biogenic magnetite particles is determined, the data can be entered into Menu #1 of the Infant ID Input touch screen display, shown in FIG. 25.

Figure 5:
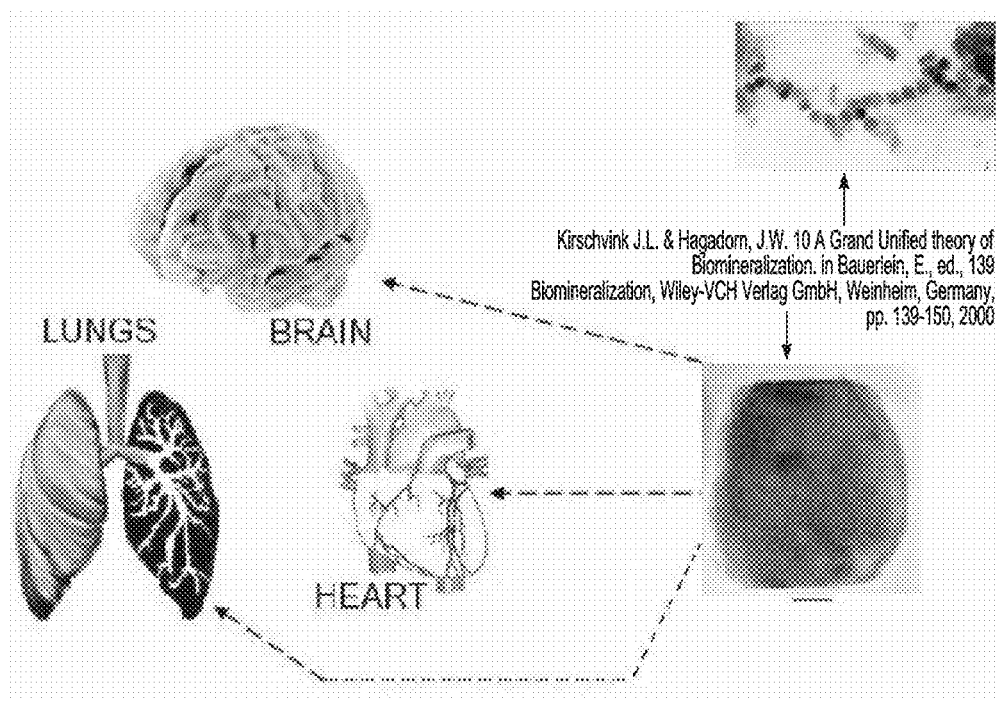
FIG. 5 illustrates details of the Magnetite maghemite crystals in a human body.

FIG. 5 illustrates details of the biogenic magnetite maghemite crystals. These nanoparticles form crystals of ferromagnetic material and interact more than a million times more strongly with external magnetic fields than do diamagnetic or paramagnetic materials. Studies have shown that the human brain and meninges contain trace amounts of ferromagnetic material. These magnetic particles in the human brain are diffusely and homogeneously distributed over all cerebral lobes, the cerebellum, basal ganglia and midbrain. Iron oxide nanoparticles are iron oxide particles with diameters between about 12 and 200 nanometers. The two main forms are magnetite ($FE_3O_4$) and its oxidized form maghemite ($\gamma$-$FE_2O_3$).

Figure 6:
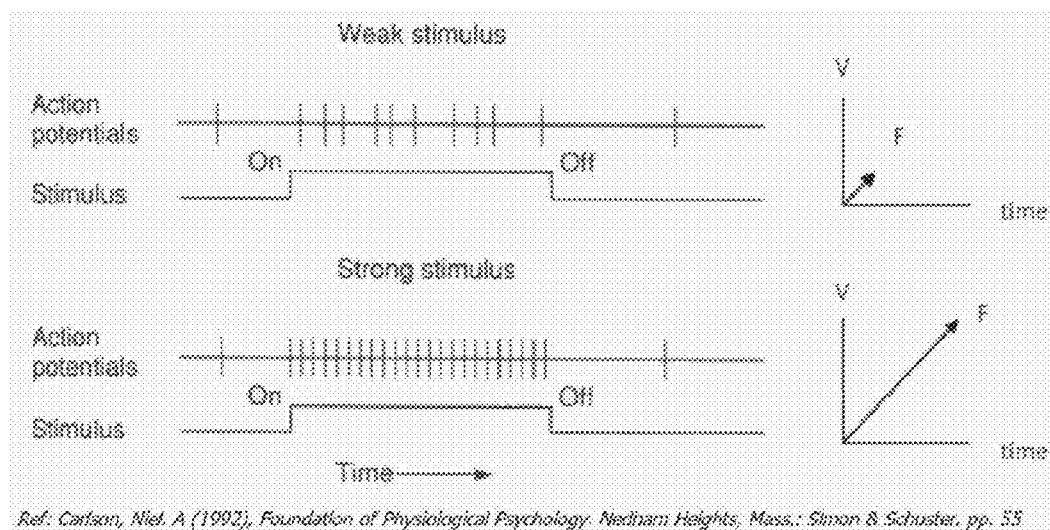
FIG. 6 illustrates a graphical view of the neuron rate law for neurons. A strong stimulus means more action potentials fire.

Magnetite maghemite is a black ferromagnetic crystal mineral form of iron oxide and interacts more than a million times more strongly with external magnetic fields than do diamagnetic or paramagnetic materials. H. Coetzee, et al., Magnetic Biomineralization in the Human Brain, Proceedings of the National Academy of Sciences, vol. 89 (1992): pg. 7683-7687. A piezoelectric effect is induced by the inductive coupling on the magnetite crystals which results in generating a voltage level shift on the voltage-gated channels of the neurons. The force (F) is enough to cause the neuron voltage threshold levels to change and cause more action potentials to fire. FIG. 6 illustrates the neuron rate law for neurons. A strong stimulus means more action potentials fire.

The infant's neuronal network is stimulated as a result of the input stimulus which is manifested by an increase in Inter Spike Interval (ISI) frequencies. An increase in ISI is a result of more neurons exceeding their voltage potential thresholds. A measureable difference in the infant's EEG frequencies can be attributed to changes in ISI frequencies.

Figure 7:
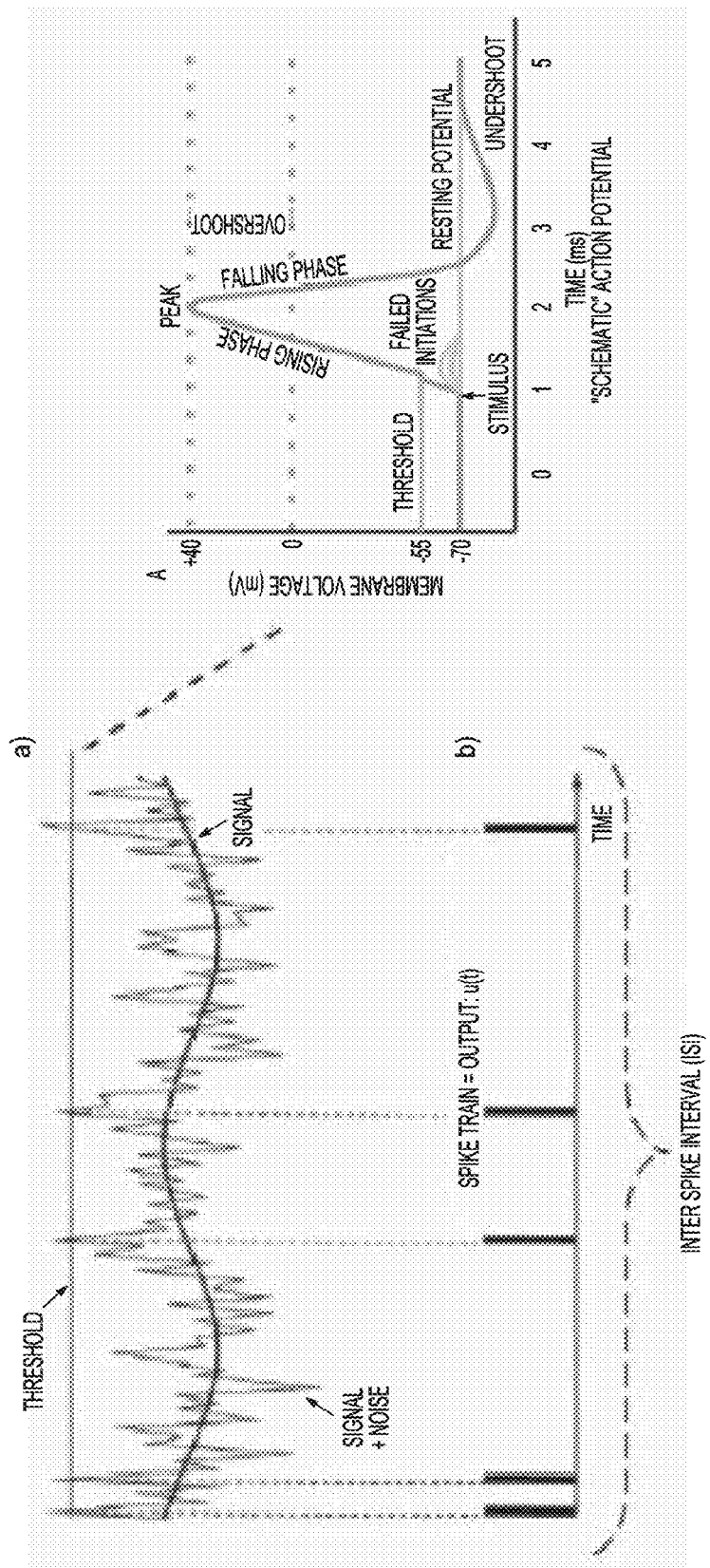
FIG. 7 illustrates a graphical view of the relationship between input stimulus and neuron firing.

FIG. 7, illustrates an overview of the relationship between input stimulus and neuron firing. In simple terms, when Stochastic Resonance noise interacts with biogenic magnetite and neurons, the result is a waveform with peaks that correspond to both the amplitude of the noise and the amplitude of the signal. In the presence of a neuronal network, these peaks add to the membrane voltage potential and cause a spike to occur at the threshold level. Notice on the left side of FIG. 7, when a spike occurs, an action potential occurs and the neuron exhibits a response as shown on right side of FIG. 7. The input stimulus must add enough voltage potential to the threshold level to make the neuron trigger and cause an action potential to spike (neuron fires). Hanggi, Peter, "Stochastic resonance in biology, ChemPhysChem 3 (2002), pg. 286.

Figure 8:
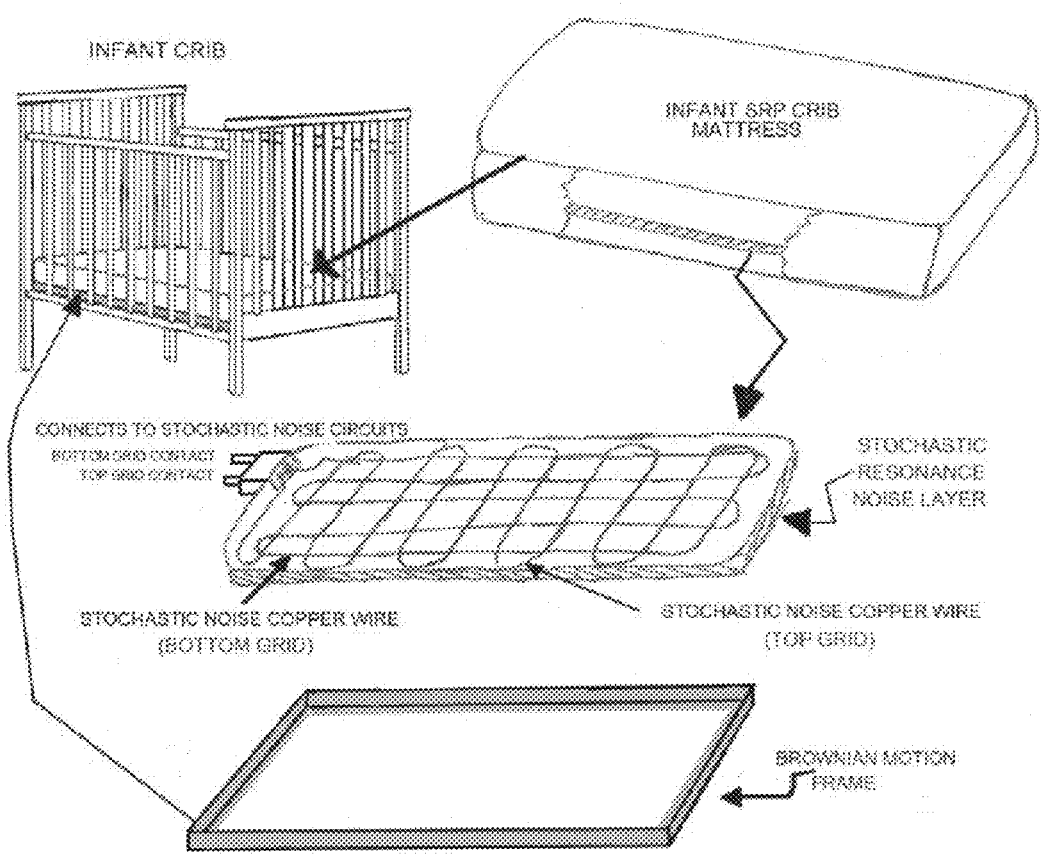
FIG. 8 illustrates an exploded view of an infant crib, features inside the SRP CRIB mattress and Brownian Motion Frame of one system embodiment of the invention disclosed herein.

The infant receives the neuronal stimulation from two grids made of copper wire which are incorporated inside the mattress. FIG. 8 illustrates two copper grids 60 and 62 sandwiched inside an infant mattress 64. One copper grid 60 is on the top and the other copper grid 62 is on the bottom.

The Stochastic Resonance noise mattress 66 sits on top of the Brownian Motion Frame 68, illustrated in FIG. 8, which will be discussed in detail in the latter part of this patent application. A Stochastic Resonance stimulus circuit generates the neuronal stimulus which consists of white noise with embedded cyclic signals. Two shielded coax wires 70 are used to connect the top and bottom copper grids to the neuronal stimulus circuit which is contained in the SRP microcontroller system.

Stochastic Resonance Stimulus Circuit

Figure 9:
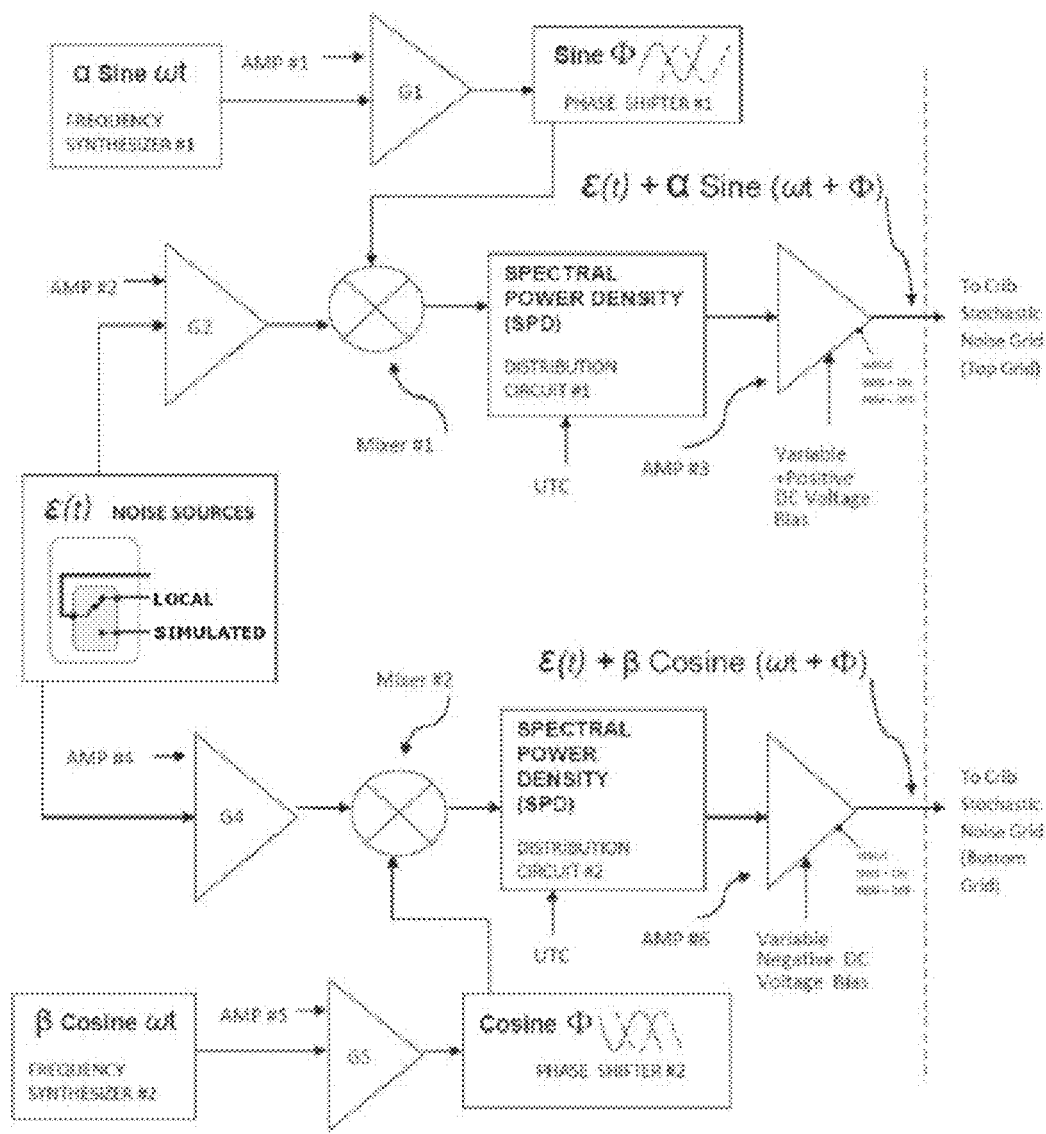
FIG. 9 illustrates one embodiment of the Stochastic Resonance Stimulus Circuit, and includes Frequency Synthesizer gain phase shift of Phase Shifter and Spectral Power Density Distribution Circuits and the DC voltage Bias of amplifiers.

FIG. 9 illustrates one embodiment of the Stochastic Resonance Stimulus Circuit. The Stochastic Resonance Stimulus Circuit consist of a white noise selection switch Frequency Synthesizer #1 and #2, gain amplifiers AMP #1, AMP #2, AMP #4, AMP #5, phase shift of Phase Shifter #1 and #2 and Spectral Power Density Distribution Circuits #1 and #2 and the DC voltage Bias of amplifiers AMP #3 and AMP #6.

The generation of the neuronal stimulus signals begins with the selection of a white noise source; E (t). The Stochastic Resonance circuit includes either a LOCAL WHITE NOISE source or SIMULATED WHITE NOISE source. The SRP microcontroller automatically selects LOCAL WHITE NOISE as the first noise source. However, in the absence of a high quality local white noise source, the SRP microcontroller selects the SIMULATED WHITE NOISE source. Normally, the level of electromagnetic white noise power is heavily influenced by diurnal and seasonal factors, as well as geographic location.

In the scientific community, it is well known that the natural source of electromagnetic white noise comes from the earth's lightning strikes which occur approximately 100 times per second. In the summer (northern hemisphere), the LOCAL NOISE SOURCE is preferred due to the richer content of spectral frequencies generated by the close proximity of lightning strikes from thunderstorms in South America, Africa and Southeast Asia. In the winter time, the earth's tilt causes a reduction in the level of electromagnetic white noise power as the proximity of lightning strikes from thunderstorms is further south. Consequently, the SRP system may select the SIMULATED WHITE NOISE source during the winter. Other factors influence the characteristics of electromagnetic white noise, such as the ionosphere D-layer on the dayside of the earth, and the disappearance of the D-layer on the night side.

After the selection of the white noise source is performed, the SRP system sends the white noise signal to two paths. In one path, the white noise signal is combined with a positive sine waveform signal [α Sine ωt+φ)], and on the other path, the white noise signal is combined with a negative cosine waveform [β Cosine ωt+φ]. The positive sine waveform signal [α Sine ωt+φ] path begins with the ϵ(t) noise source entering amplifier AMP #2. At the same time the negative cosine waveform [β Codine ωt+φ] path begins with the ϵ(t) noise source entering amplifier AMP #4. The SRP system sends the white noise output of AMP #2 to MIXER #1 where it is combined with the positive sine waveform signal of FREQUENCY SYNTHESIZER #1 [α Sine ωt+φ]. Likewise, the SRP system sends the ϵ(t) white noise output of AMP #4 to MIXER #2 where it is combined with the negative cosine waveform signal of FREQUENCY SYNTHESIZER #2; [βCosine ωt+φ].

The output of MIXER #1 now contains white noise embedded with the cyclic positive sine waveform of FREQUENCY SYNTHESIZER #1, which can be expressed as [ϵ(t)+α Sine ωt+φ]. The output of MIXER #2 now contains white noise embedded with the cyclic negative waveform of FREQUENCY SYNTHESIZER #2, which can be expressed as [ϵ(t)+β Cosine ωt+φ]. The next process is for the output of MIXER #1 to enter the SPECTRAL POWER DENSITY Distribution Circuit #1, and for the output of MIXER #2 to enter the SPECTRAL POWER DENSITY Distribution Circuit #2. The output of the SPECTRAL POWER DENSITY Distribution Circuit #1 enters AMP #3, and the output of the SPECTRAL POWER DENSITY Distribution Circuit #2 enters AMP #6. Finally, the neurological stimulus signal [ϵ(t)+α Sine ωt+φ] from AMP #3 is sent to the top Stochastic Resonance noise grid via the copper wire, which is inside the infant's crib mattress. Likewise, the neurological stimulus signal [ϵ(t)+β Cosine ωt+φ] from AMP #6 is sent to the bottom Stochastic Resonance noise grid via the copper wire inside the infant's mattress.

Figure 10A:
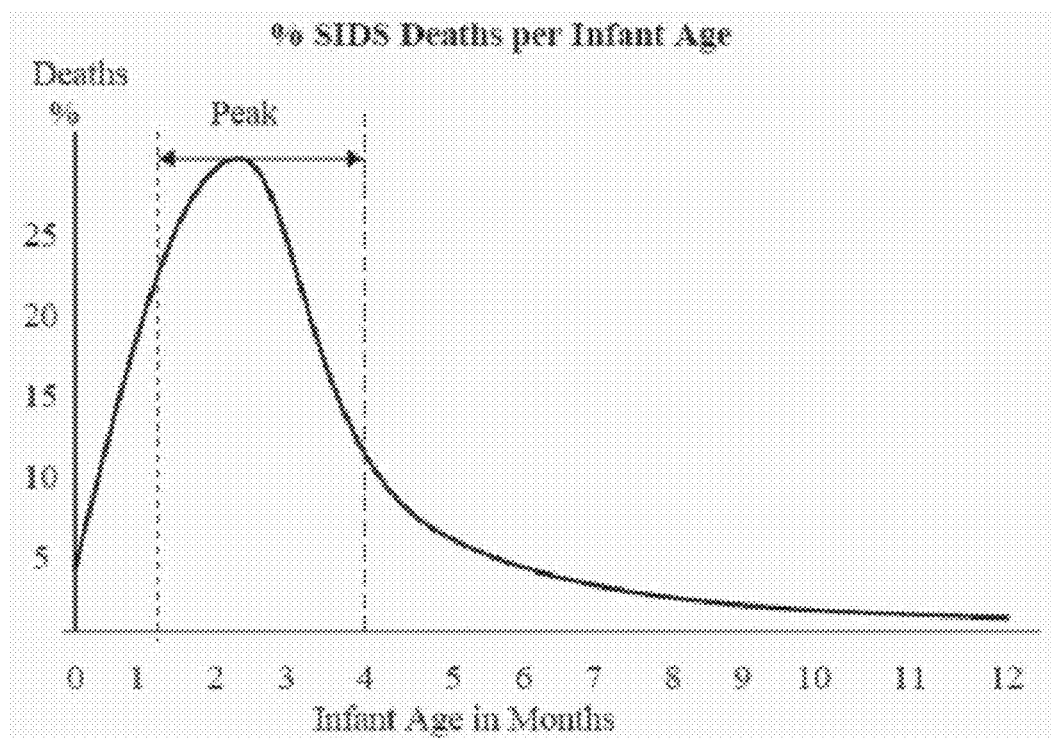
FIG. 10A illustrates a graphical view of the percentage of SIDS deaths by infant age per month based on historical data of SIDS documented deaths.

The SRP system considers the characteristic signature of the SIDS timeline for the twelve months that an infant may be put at risk of SIDS. FIG. 10A illustrates a diagram with the percentage of SIDS deaths by infant age per month based a historical data of SIDS documented deaths. The peak months for SIDS deaths occur between the 1$^{st}$ and 4$^{th}$ months of an infant life.

FIG. 10B shows the SIDS Risk Kurtosis Scale. The numeric values are weighted to show a SIDS Risk Kurtosis Scale number from #16 (being the highest) to number #1 (being the lowest). These numeric values are dependent upon the infant's gender as well as the infant's sleep state (REM or SWS). FIG. 10B also shows how the winter and summer seasons, as well as the time of day, can be used as variables to generate a SIDS Risk Kurtosis Number. Additionally, the SRP system performs a best fit correlation between the infant's date of birth (DOB) and the peak SIDS months by using the Coordinated Universal Time (UTC) from NIST time servers. The mean goal of the SRP microcontroller is to provide optimum neuronal stimulus outputs to the infant based on matching the SIDS timeline, modified with the SIDS Risk Kurtosis Scale, to apply a time distributive output based on skewness and kurtosis coefficients.

The operation and performance of amplifiers AMP #1-AMP #6 and PHASE SHIFTER #1, PHASE SHIFTER #2 and SPECTRAL POWER DENSITY Distribution Circuits #1 and #2 are controlled by the SRP microcontroller based on the Rayleigh Probability Density Function. Equation 1.0 illustrates a simplified variant of the Rayleigh Probability Density Function (PDF):

$$f(x; \sigma) = \frac{x}{\sigma^2} e^{-x^2/2\sigma^2}, x \geq 0,$$

Equation 1.0 Rayleigh Probability Density Function (PDF)

Figure 11:
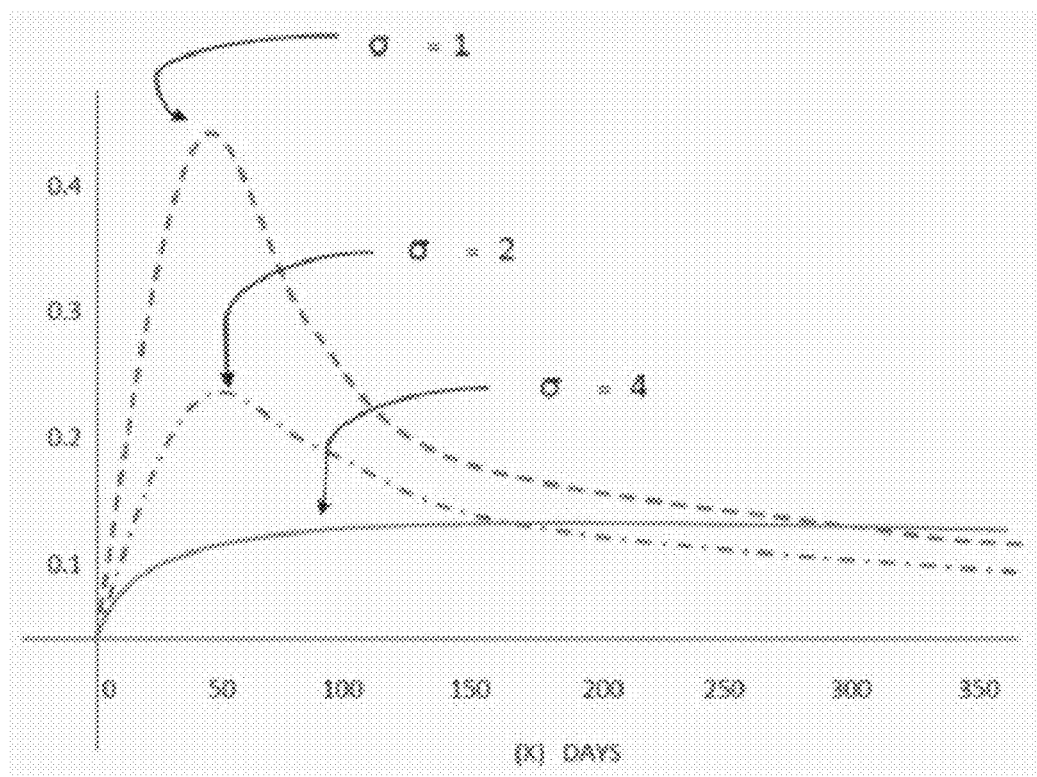
FIG. 11 illustrates a graphical view of the Rayleigh Probability Density Function (PDF), plotting three different mode values.
Figure 27:
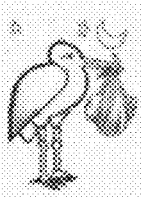
FIG. 27 illustrates Menu #3, SIDS Survival Matrix including data on Stochastic Resonance, Brownian Motion, Sleep State Ratio, Biogenic Magnetite, Rayleigh (PDF).
Figure 28:
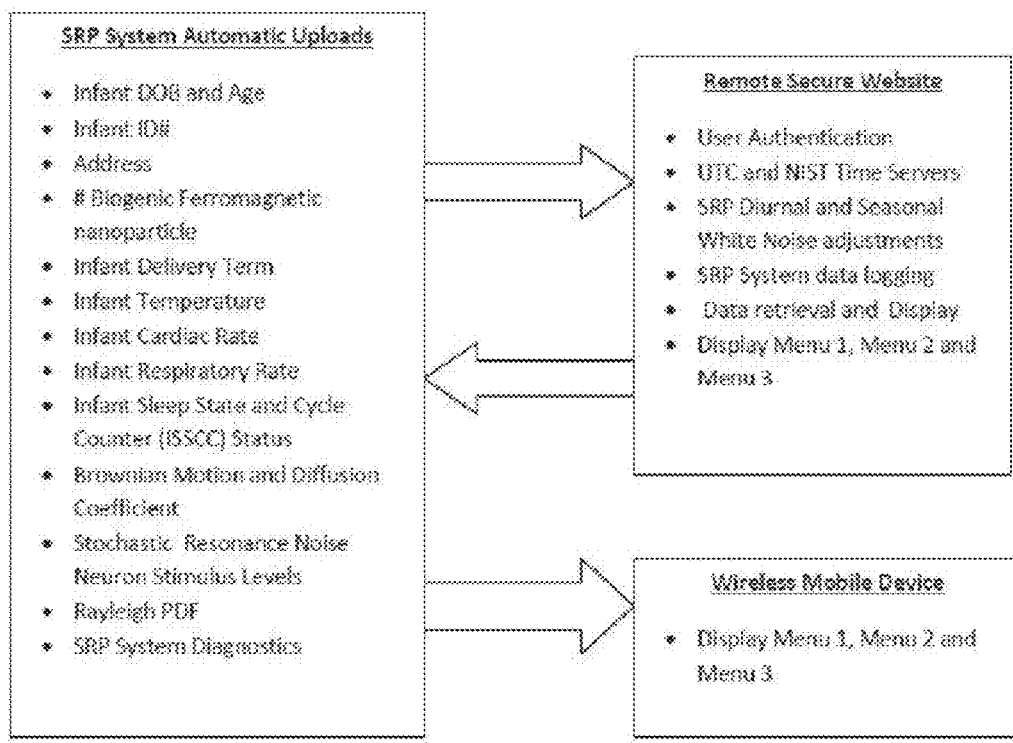
FIG. 28 illustrates the information between the SRP, Wireless Mobile Devices and the Remote Website.

FIG. 11 illustrates a Rayleigh Probability Density Function (PDF) Plot with three different mode values of σ=1, σ=2 and σ=4. During the first four months of the infants life the SRP microcontroller uses a lower mode value of a because this produces a skewness and kurtosis curve which, most closely matches the SIDS timeline for these early months. As the infant ages, the probability of a SIDS related incident will start to decrease after the fourth month. After the fourth month the SRP system sets σ=2 and may on occasion; either decrease or increase the value slightly depending on the quality of the power density and the richness of the frequency spectra of the white noise available in the area near the crib. The SRP system sends the values of the skewness and kurtosis curves, PDF mode and white noise spectral power as well as the value of the voltages and frequencies of the Stochastic Resonance Noise signals to Menu 3 of the SIDS Survival Matrix display as shown in FIG. 27 and to the remote secure website, one screen of which is shown in FIG. 28.

The SRP system continuously monitors the UTC from NIST time servers and determines the best value for a as a function of the SIDS timeline and the infant's date of birth (DOB). At approximately the sixth month, the value is set, σ=4. As time progresses the probability of a SIDS related incident will continue to decrease and the SRP system will continue to increase the value of a accordingly.

Figure 12:
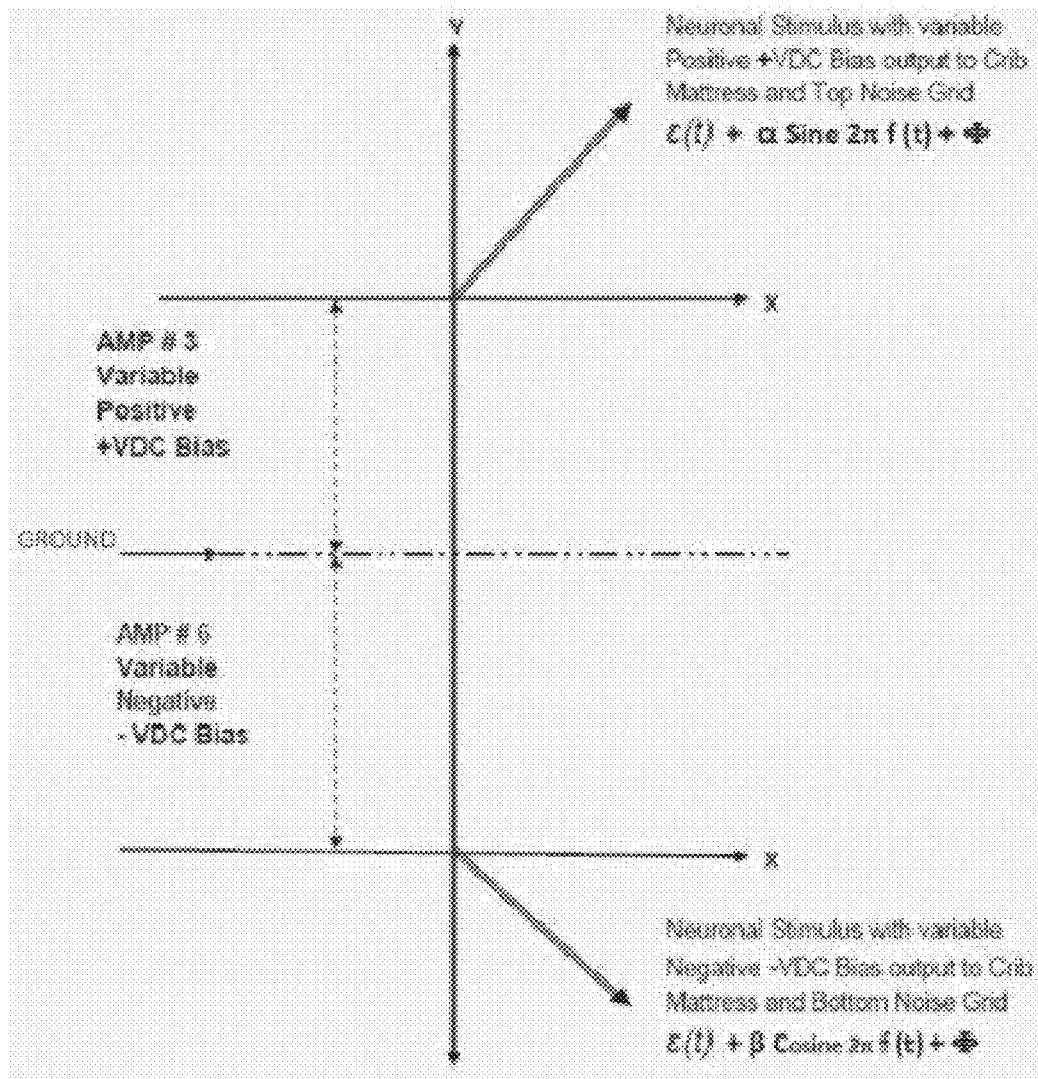
FIG. 12 illustrates a schematic view of the Dawn-Dusk variable output of amplifiers.
Figure 23:
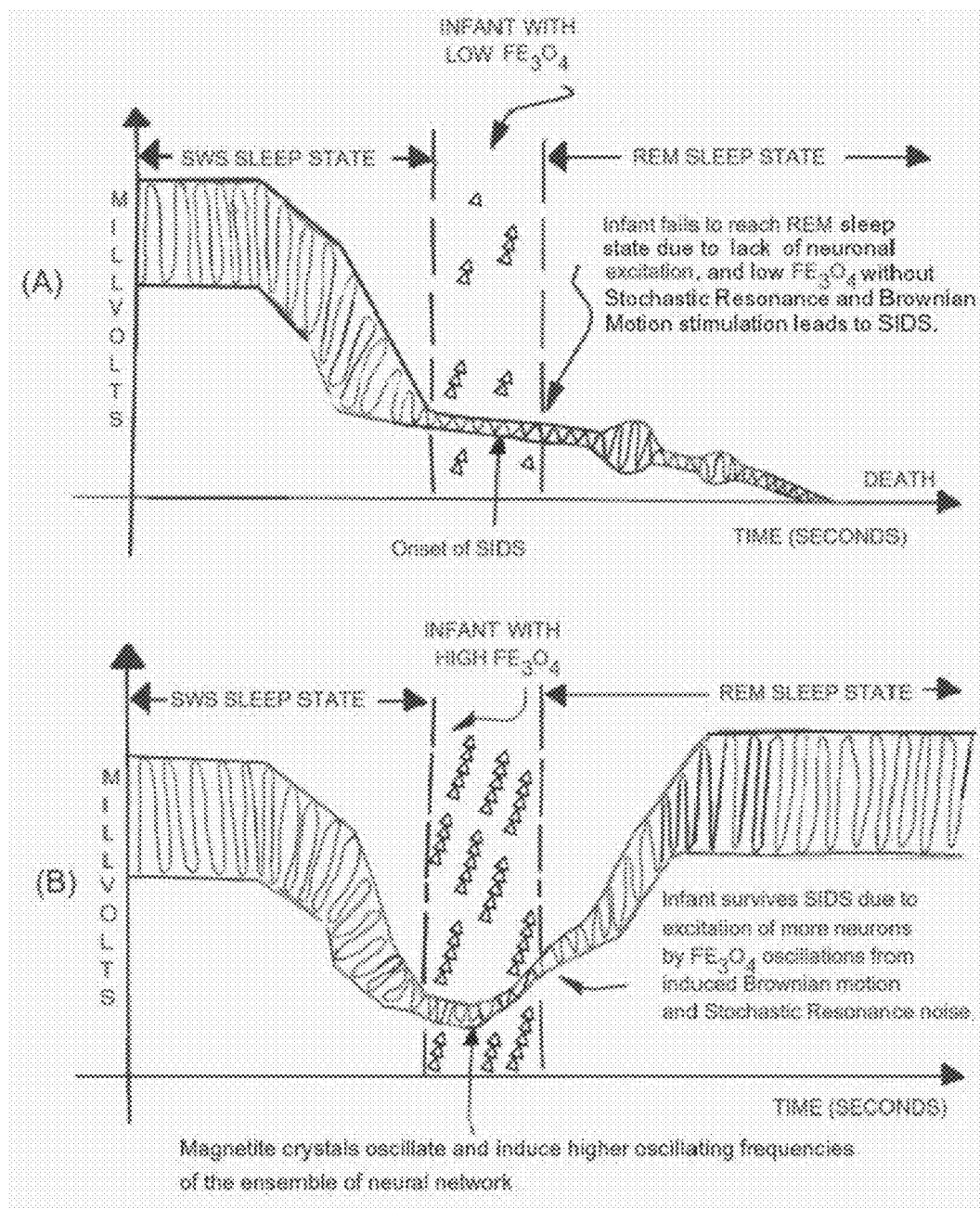
FIG. 23 illustrates Infants with high and Low $Fe_3O_4$ with oscillations from induced Brownian Motion and Stochastic Resonance noise.

Further, if the infant has lower levels of biogenic magnetite, it may not have the advantage of Brownian Motion to excite neuronal excitation. This could result in an inability of the infant to successfully transition from the SWS sleep state to the REM sleep state as shown in FIG. 23 subpanel (A). FIG. 12 illustrates the Dawn-Dusk variable output signals at the output of AMP #3 and AMP #6.

Figure 13:
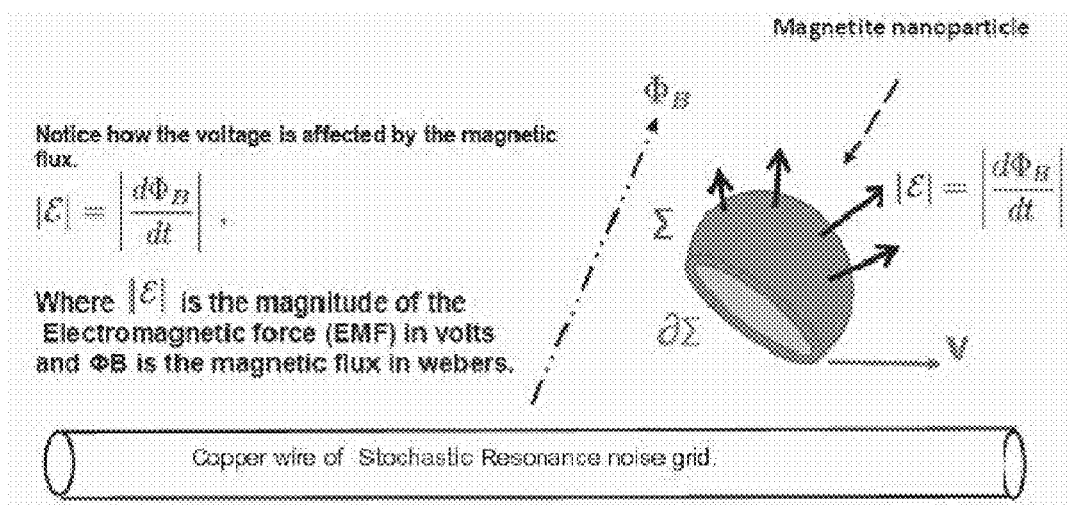
FIG. 13 illustrates a graphical representation of the effects of the electromagnetic force on the infant's biogenic magnetite.

The SRP microcontroller makes seasonal and Dawn/Dusk adjustments to the DC voltage bias to AMP #3 and AMP #6 over time. The voltage level for AMP #3 is decreased from a positive value to zero at dusk. The voltage level for AMP #6 is increased from a negative value to zero at dawn. The starting voltage values for the DC bias are a function of the kurtosis coefficient. The shape of the DC voltage curve over time is derived from the skewness coefficient and is a function of the σ mode value. FIG. 13 is the graphic representation of the effects of the electromagnetic force on the infant's biogenic magnetite. The SRP system via the copper wire grids induces a magnetic flux $\Phi_B$ through the infant's mattress.

According to Faraday's law of induction, a force applied by magnetic flux $\Phi_B$ will induce an electric voltage |ϵ| on a given particle. In the case of SIDS, this particle is the biogenic magnetite inside the infant's body. Therefore, the SRP system with the Stochastic Resonance Noise (and Brownian Motion) serves as a neuronal stimulus and effects the infant's magnetite nanoparticle in such a way as to increase the random openings and closings of ion channels of neurons in the area near the biogenic magnetite, thereby causing more neuron action potentials to fire and increasing the Inter Spike Interval frequencies of the infant's ensemble of neurons. The increase in ISI frequencies, in turn, affect the infant's homeostasis, which prevents interruptions to the infant's cardiac and respiratory rhythms and reduces the risk of death due to SIDS. The SRP has an Infant Sleep State Cycle Counter (ISSCC) circuit which turns ON the Stochastic Resonance Noise circuit during the time the infant is in the Slow Wave Sleep (SWS) state. The ISSCC circuit turns the Stochastic Resonance Noise Circuit OFF during the time that the infant is in the Rapid Eye Movement (REM) sleep state.

Infant Sleep States and Cycle Counter (ISSCC)

SRP system embodiments include an Infant Sleep State Cycle Counter (ISSCC) 48 as shown in FIG. 3. The IS SCC 48 keeps track of the duration and numbers of both of the infant's SWS and REM sleep states. SRP system embodiments determine when the infant is sleeping by differentiating changes in infant body temperature via the thermal image camera and changes in Cardiorespiratory rates via the Doppler Ultrasound transducer 46. SRP system embodiments collect an infant's temperature and cardiorespiratory data and save it in memory. The SRP microcontroller 42 then performs a cross correlation of the saved temperature and Cardiorespiratory data to derive epochs of SWS and REM sleep states.

Figure 26:
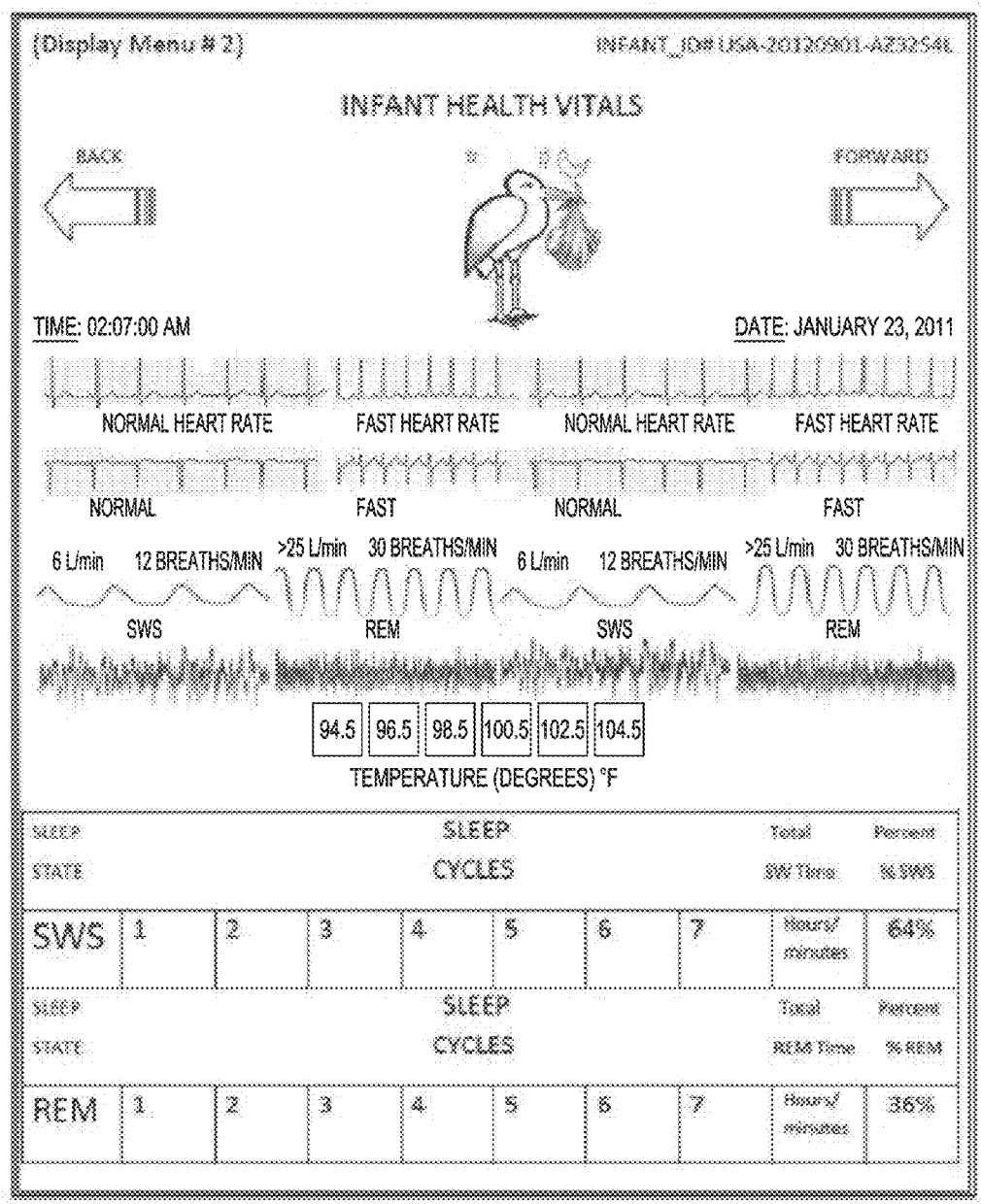
FIG. 26 illustrates Menu 2 Infant's Health vitals, Cardiorespiratory data and Sleep State.

Normally, the infant's temperature increases slightly during the time that the infant is in the REM sleep state and at the same time the cardiac rate increases. The breathing rate also increases during the REM sleep. The ISSCC circuit counts this episode as one REM sleep epoch. When the infant transitions from the REM sleep state to the SWS sleep state, the temperature decreases slightly and this is detected by color changes from the thermal image camera. The Doppler Ultrasound transducer then detects slower cardiac and breathing rates. When the SRP microcontroller 42 correlates the lower change in temperature and the slower cardiac and breathing rates, this is counted as one SWS sleep epoch. This information is then sent to three locations: first it is sent to the ISSCC circuit, and then it is sent as data to Infant Health Vitals (Menu 2 of the display as shown in FIG. 26). Finally, it is sent, for some embodiments, to a remote secure website via the internet. The ISSCC controls the Stochastic Resonance Noise Circuit and the Brownian Motion Circuits which are described in detail herein.

Thalamocortical Neurons, SIDS and Sleep States/Cycles

Figure 14:
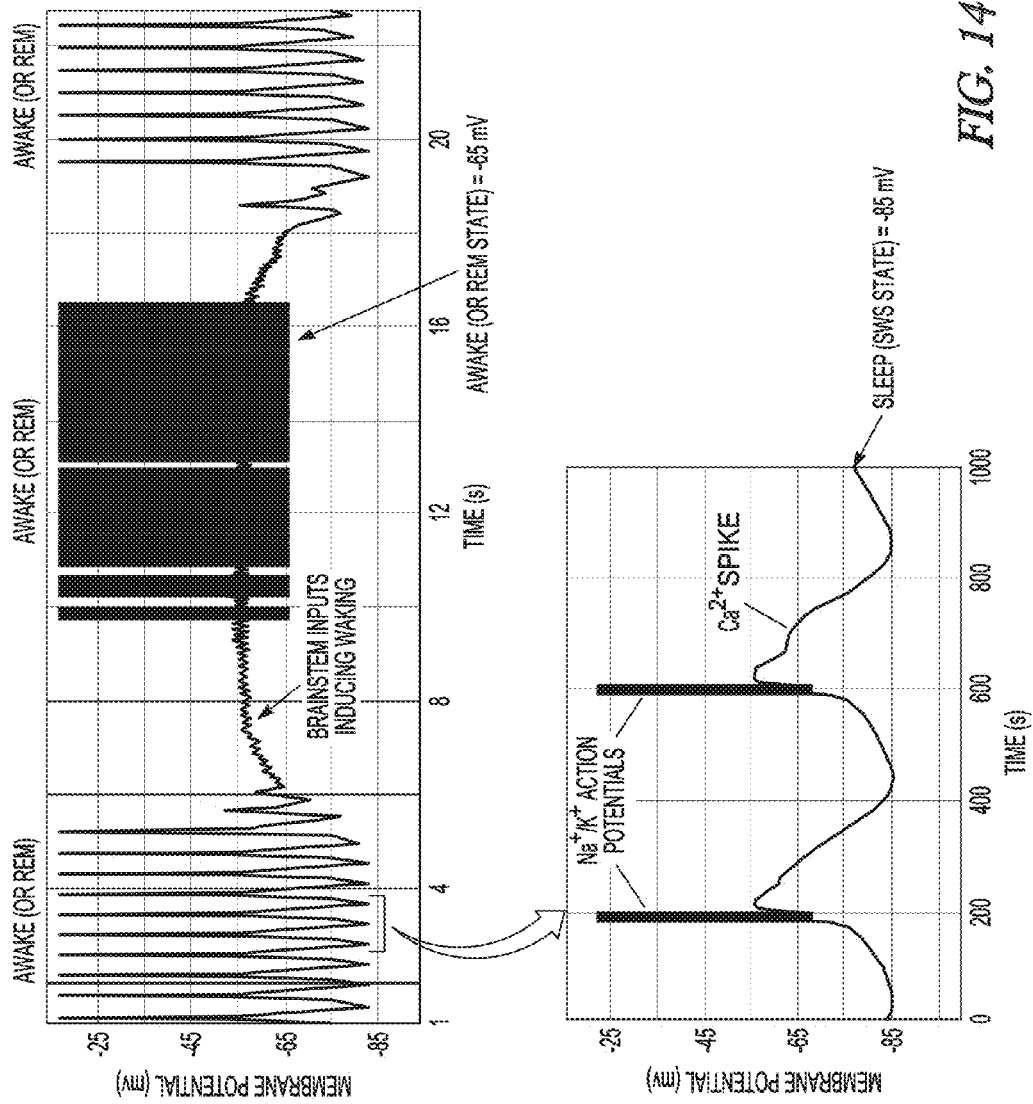
FIG. 14 illustrates a schematic view of EEG voltage and frequency differences in brain activity during wake and sleep stages.

During the SWS sleep state, it is believed that the frequency of Inter Spike Intervals decreases more for infants at risk of SIDS, due to lower neuronal voltage threshold levels at the transmitter and receptor synaptic junctions. This causes a lower number of action potentials to fire. It is during this time that the homeostasis system is most challenged and the risk of SIDS is the highest. Throughout the millions of years of human evolution the thalamocortical neurons evolved to control sleep and wake stages. The thalamocortical neurons have two stable electrophysiological states. FIG. 14 illustrates the EEG voltage and frequency differences in brain activity during wake and sleep stages.

Figure 15:
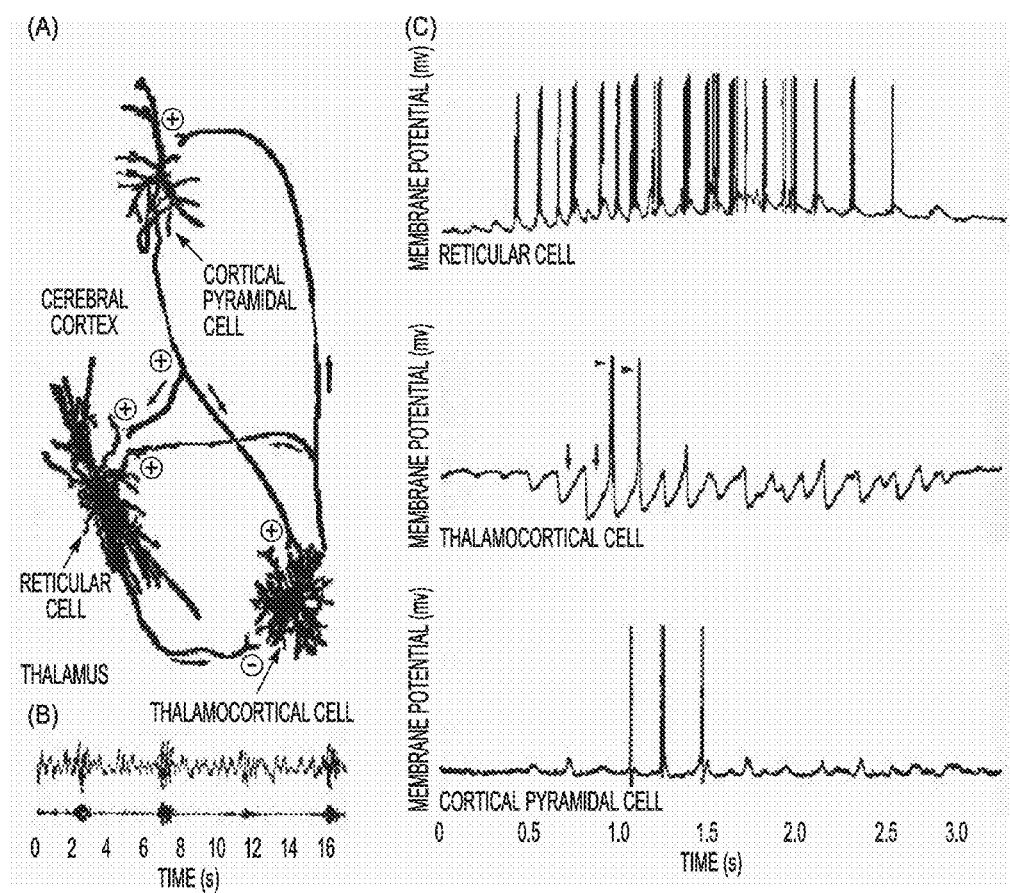
FIG. 15 illustrates a graphical view of the tonic firing state, when thalamocortical neurons transmit information to the cortex that matches the spike trains encoding peripheral stimuli.

During sleep, the thalamocortical neurons are in an intrinsic oscillatory state. In the oscillatory/bursting mode, the neurons in the thalamus become synchronized with those in the cortex, essentially "disconnecting" the cortex from the outside world. This disconnection of the cortex translates the body, becoming physically immobile during sleep. During the SWS sleep state, the EEG recordings show the lowest frequency and the highest amplitude. When the infant is awake, the thalamocortical neurons are in tonic active state. FIG. 15 illustrates the thalamocortical neurons showing oscillatory mode in a sleep state and tonically active mode in an awake state. In the tonic state, the thalamocortical neurons transmit information to the cortex that matches the spike trains encoding peripheral stimuli.

It is known that bursts of action potentials are evoked only when the thalamocortical neuron is hyperpolarized sufficiently to activate low-threshold calcium channels. These bursts account for the spindle activity seen in EEG recordings in stages II and III sleep. Depolarizing the cell either by injecting current or by stimulating the reticular activating system transforms this oscillatory activity into a tonically active mode (ref. Purves D. Augustine G J, Fitzpatrick D, et al, Neuroscience, $2^{nd}$ Edition Thalamocortical Interactions, Sinauer Associates). (FIG. 28.9 and FIG. 28.10) Purves D, Augustine GJ. Fitzpatric D., et al. (ed.) The SRP System makes use of these medical findings to derive epochs of SWS and REM sleep states via the use of the thermal image camera and the Doppler Ultrasound transducer.

Figure 16:
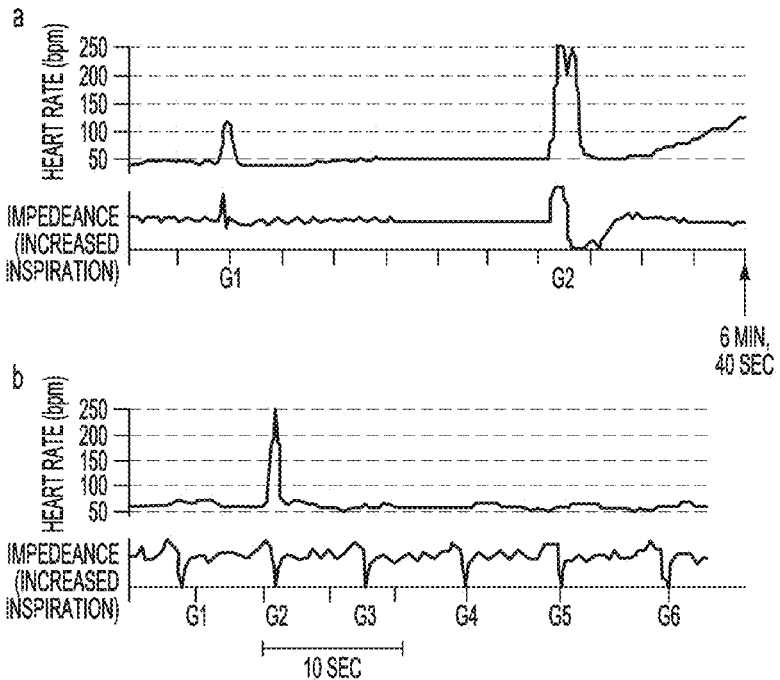
FIG. 16 illustrates a graphical view of the Cardiorespiratory Recordings in Infants, and the Results of Successful and Unsuccessful Auto resuscitation.
Figure 16:
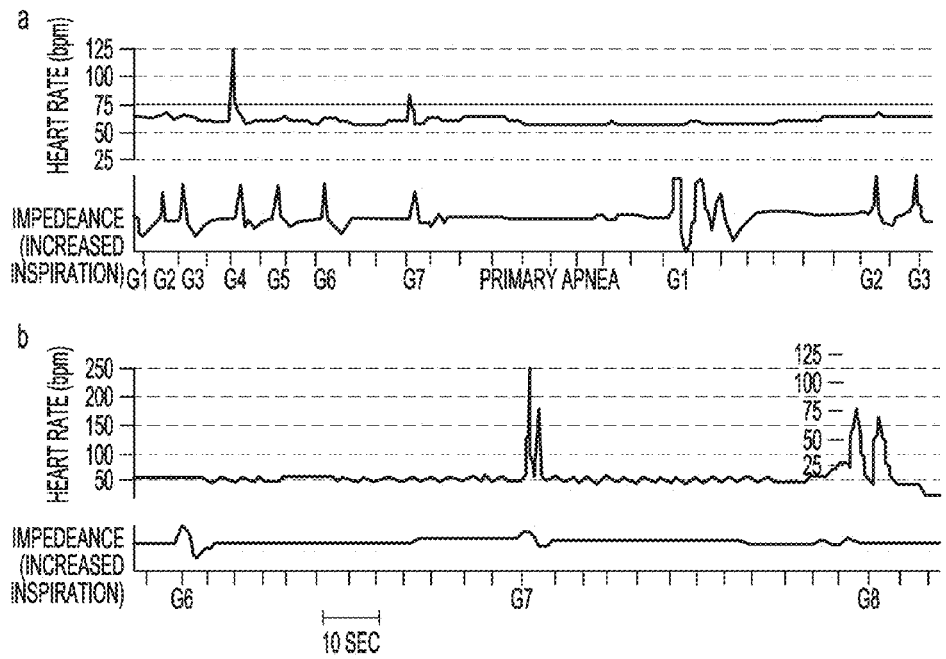

Most medical studies on SIDS agree that the underlying mechanism leading to SIDS are the result of neurological deficiencies inherited in the infant which pose adaptive challenges to the infant's cardiorespiratory system during sleep. FIG. 16 illustrates the Cardiorespiratory Recordings in Infants, Showing the Results of Successful and Unsuccessful Auto resuscitation.

"Complete autoresuscitation (Panel A) is compared with ineffectual gasping (Panel B) in cardiorespiratory recordings from infants who died suddenly while being monitored at home. In Panel A, the tracing starts with a gasp (G1), which is followed by a gradual increase in the heart rate (subpanel a). The second gasp (G2) results in an increased heart rate, at more than 100 beats per minute. After an interruption of 6 minutes 40 seconds, eupneic breaths are noted (subpanel b). Each large breath (B1-B6) is preceded and followed by smaller breaths. Larger breaths may be sighs. In Panel B, hyperpneic breaths (B1-B7) are followed by 35 seconds of primary (hypoxic) apnea (subpanel a). Gasps (G1-G3) follow this apnea. G1 is an abnormally complex, triple gasp. A period of terminal gasps (G6-68) occurs about 10 minutes after the onset of primary apnea, with decreasing amplitude and altered configuration (subpanel b). SIDS denotes sudden infant death syndrome". "The Sudden Infant Death Syndrome," New England J. of Medicine, Aug. 20, 2009: 361(8) pg. 795-805; [doi: 10.1056/NEJMra0803836] Hannah C. Kinney, M.D. and Bradley T. Thach, MD.

SRP System and Serotonin (5HT-1A) Deficiencies

Figure 17:
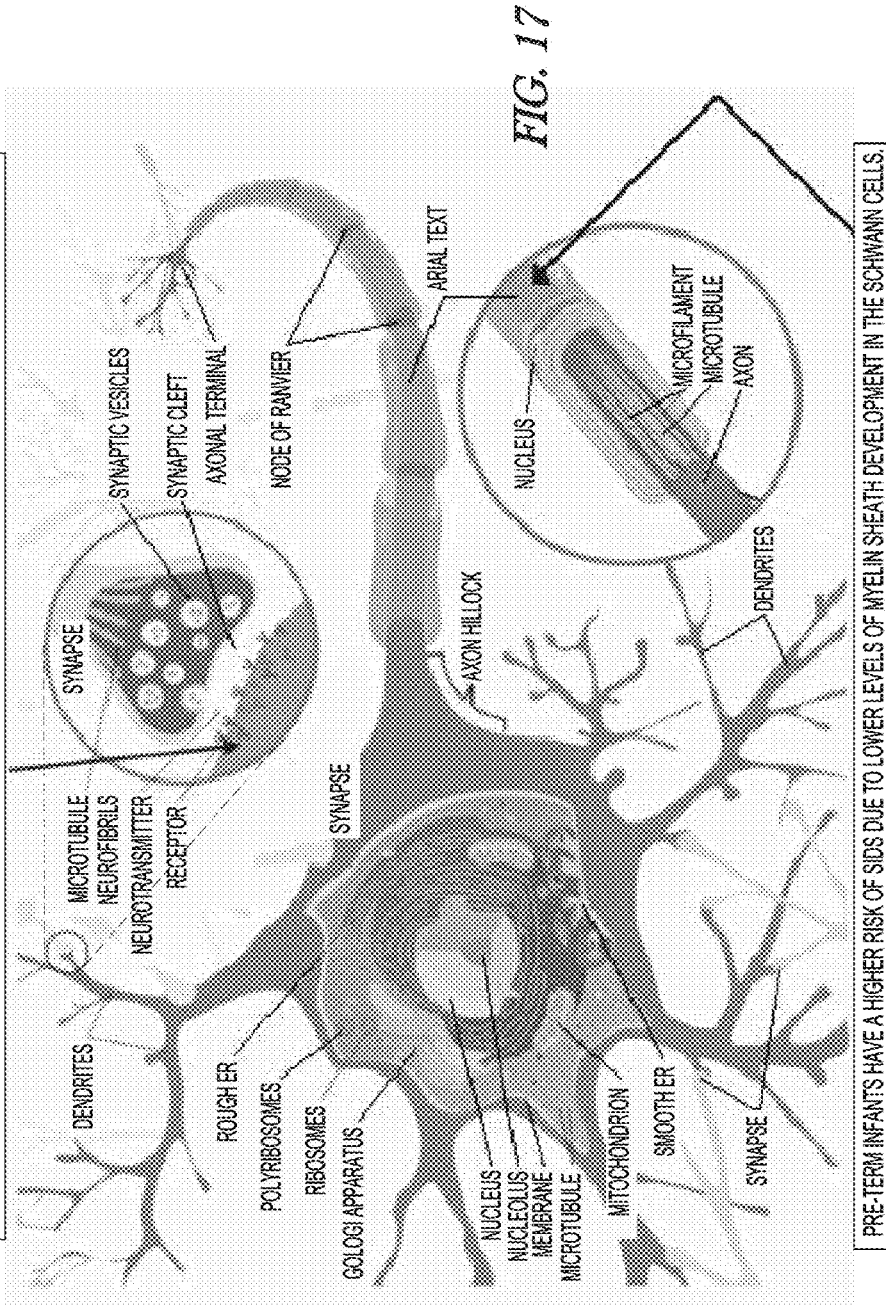
FIG. 17 illustrates a perspective view of the location of serotonin and the Myelin Sheath development in the Schwann cells.

Medical data suggests that infants that have died of SIDS have deficiencies in serotonin hydroxytryptamine type 1A (5HT-1A). These deficiencies in serotonin translate to lower voltage thresholds at the synaptic junctions. Additionally, infants that have died of SIDS show slower development in Schwann cells and lower levels of myelin. The speed of action potential (neuron firing) is directly dependent on the level of the myelin sheath maturation of the Schwann cell and synaptic threshold voltage levels. FIG. 17, illustrates the detail of the location of serotonin and the Myelin Sheath development in the Schwann cells.

The speed of the action potential propagation is faster in myelinated cells compared to unmyelinated cells. The SRP system can not affect faster development of the myelin sheath; however, the SRP can influence the overall Inter Spike Interval (ISI) firing frequencies on the infant's neuron network by inducing more action potentials to fire. These ISI in turn affect the functioning of the homeostasis system. Failure of the homeostasis system can have destructive consequences on the critical timing of the cardiac and respiratory system in those infants with neurological deficiencies.

During the first year, the infant's head grows at a phenomenal rate due to the tremendous number of new neurons created. The new neurons must quickly transform into excitatory or inhibitory neurons and join other existing clusters of oscillating neuronal networks. The cumulative and dominate oscillation frequency of the new neuronal network is heavily influenced by the neighboring sets of attractor neurons and can be described as a "Strange Attractor" in the realm of 3D manifolds.

Figure 18:
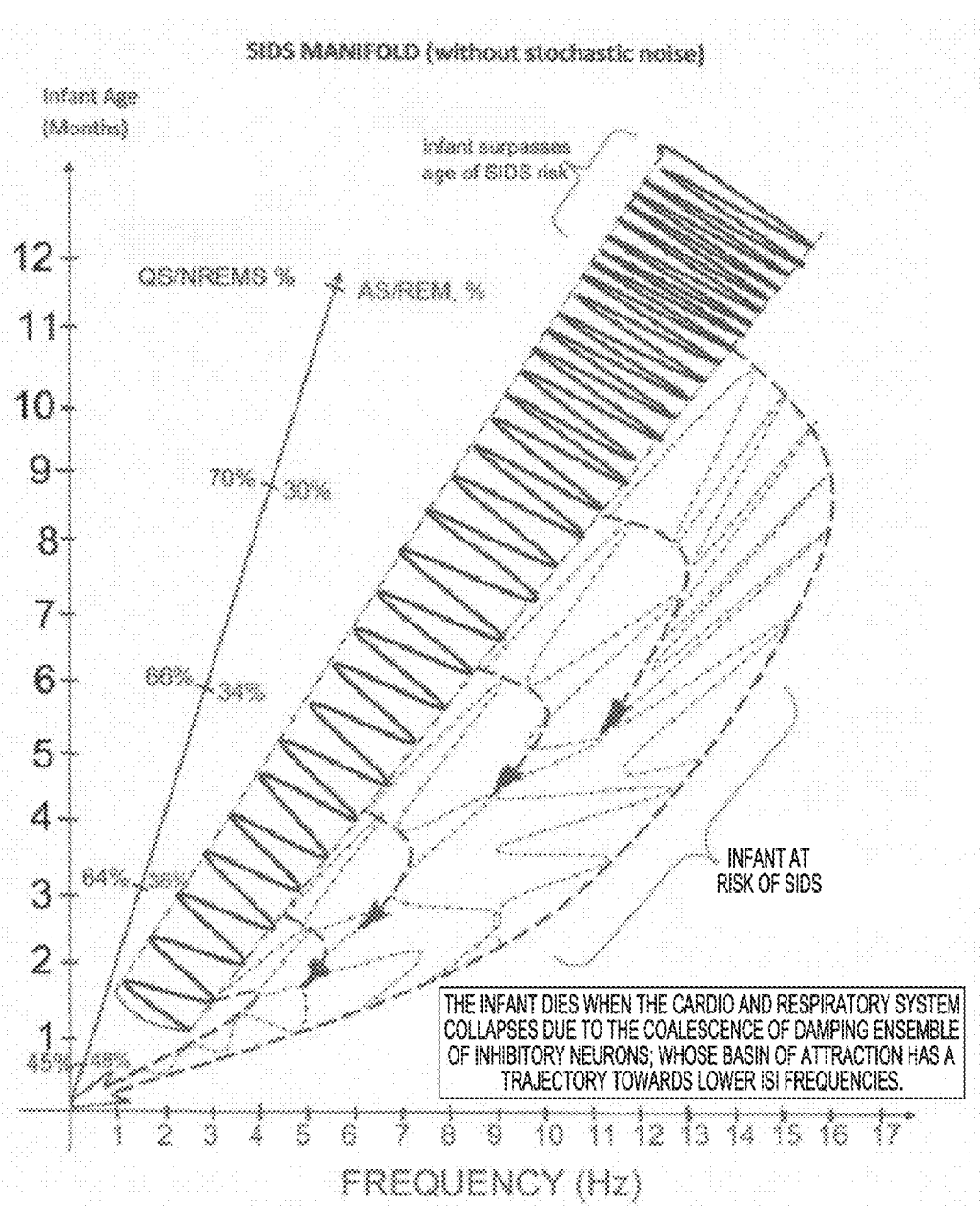
FIG. 18 illustrates a simplistic representation of neuronal manifolds. As the infant ages, the amount of time spent in the SWS sleep state increases and the power density also increases for frequencies within the 12 Hz to 14 Hz band.

FIG. 18 illustrates a simplistic representation of neuronal manifolds. As the infant ages, the amount of time spent in the SWS sleep state increases and the infant's EEG power density also increases for frequencies within the 12 Hz to 14 Hz band. Normally, over time epochs of SWS and REM sleep states become less chaotic as neuronal networks mature and the growth rate of new neurons slows. However, SIDS cases, the newly created neurons may be deficient in serotonin (5-HT) lacking enough synaptic threshold voltages to join those groups of higher oscillating neuronal networks. Because these oscillations in turn provide the framework of frequencies needed by the autonomic nervous system, the infant becomes at risk for SIDS due to a coalescence of damping ensemble of inhibitory neurons, with a basin of attraction that has a trajectory towards lower ISI frequencies. For SIDS victims, neuronal bifurcations do not succeed in increasing the Inter Spike Interval frequencies and the infant's homeostasis fails, resulting in interruptions to the cardiac and respiratory rhythms.

Infant Brownian Motion Frame

Brownian Motion at the neuronal synaptic level is clinically known to induce more action potentials to fire due to the chaotic nature of neuronal noise. The SRP system and the infant Brownian Motion frame is designed to take advantage of the effects of Brownian Motion at the neuronal level and help reduce the incidence of SIDS deaths. The details of the effects of Brownian Motion can be described by the diffusion coefficient (D) of Equation 2.

$$D = \frac{k_B T}{6\pi\mu r} \quad \text{Equation 2}$$

Where D=is the Diffusion Coefficient,
  $k_B$ is Boltzmann's constant,
    T is the temperature,
    $\mu$ is viscosity of the infant's cranial fluid,
    r is the radius of the ferromagnetic (magnetite) particle in nanometers
  According to Einstein an alternative method to describe the diffusion coefficient can be shown in Equation 3 (Einstein's Diffusion Coefficient Equation).

$$<|X[t-dt]-X[t]|^2>=2D[dt] \quad \text{Equation 3}$$

Where; D is the diffusion coefficient, and X (t) is the location of particle X (ferromagnetic) at time (t) and X (t−dt) is the location of particle X at some time (t−dt). We can rewrite equation 3 to show the diffusion coefficient (D) and mean squares in a form that describes the movement of the particle as a deviation in a given direction as shown in Equation 4:

$$D = \frac{\overline{\Delta}^2}{2t} \quad \text{Equation 4}$$

Figure 19:
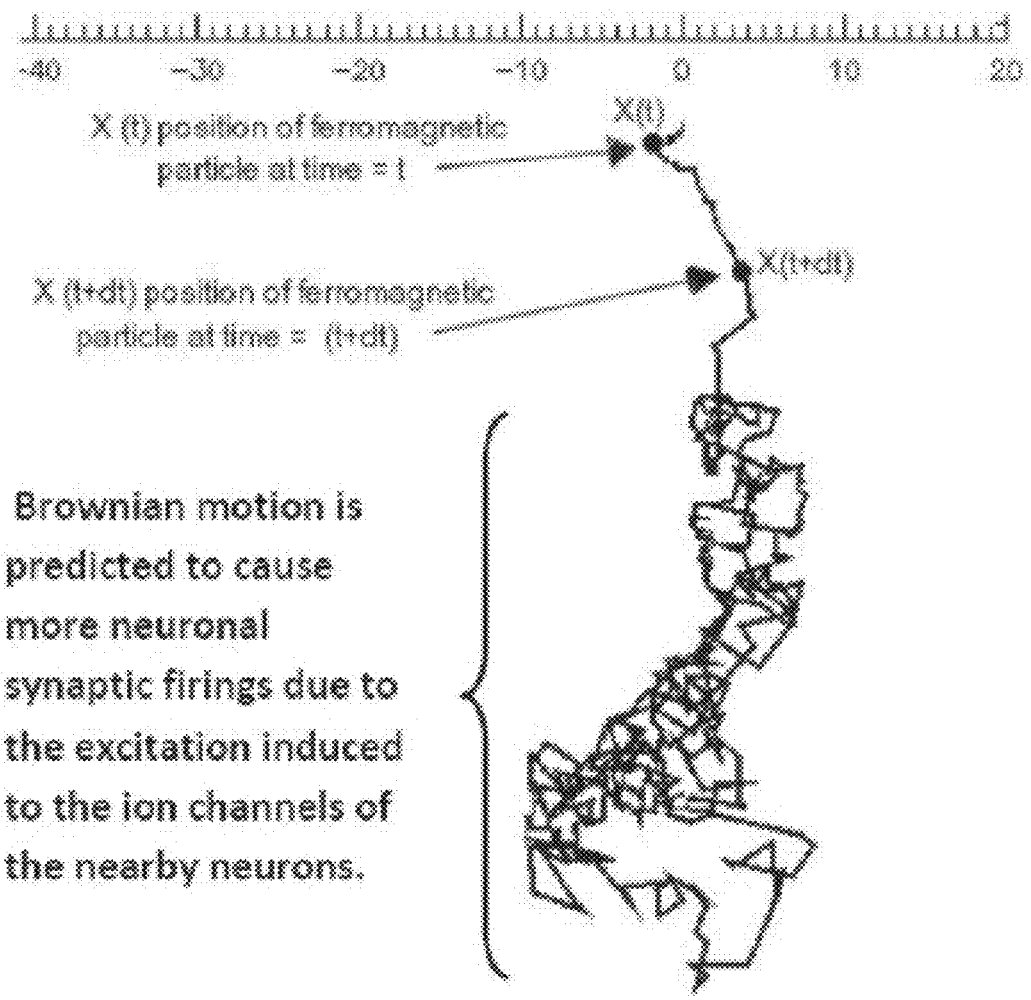
FIG. 19 illustrates a graphical view of the effects of Brownian Motion on a ferromagnetic nanoparticle which is suspended in fluid, such as the cranial fluid of an infant.

Where: $\overline{\Delta}^2$ is the mean square of the deviation in a given direction in time t. FIG. 19, is a graphic representation of the effects of Brownian Motion on a ferromagnetic nanoparticle which is suspended in fluid, such as the cranial fluid of an infant. Notice: the particle has a greater degree of freedom in the fluid when Brownian Motion is applied. The SRP system embodiments with the Brownian Motion are able to cause more action potentials to fire due an increased excitation induced to the ion channels of nearby neurons.

Figure 20:
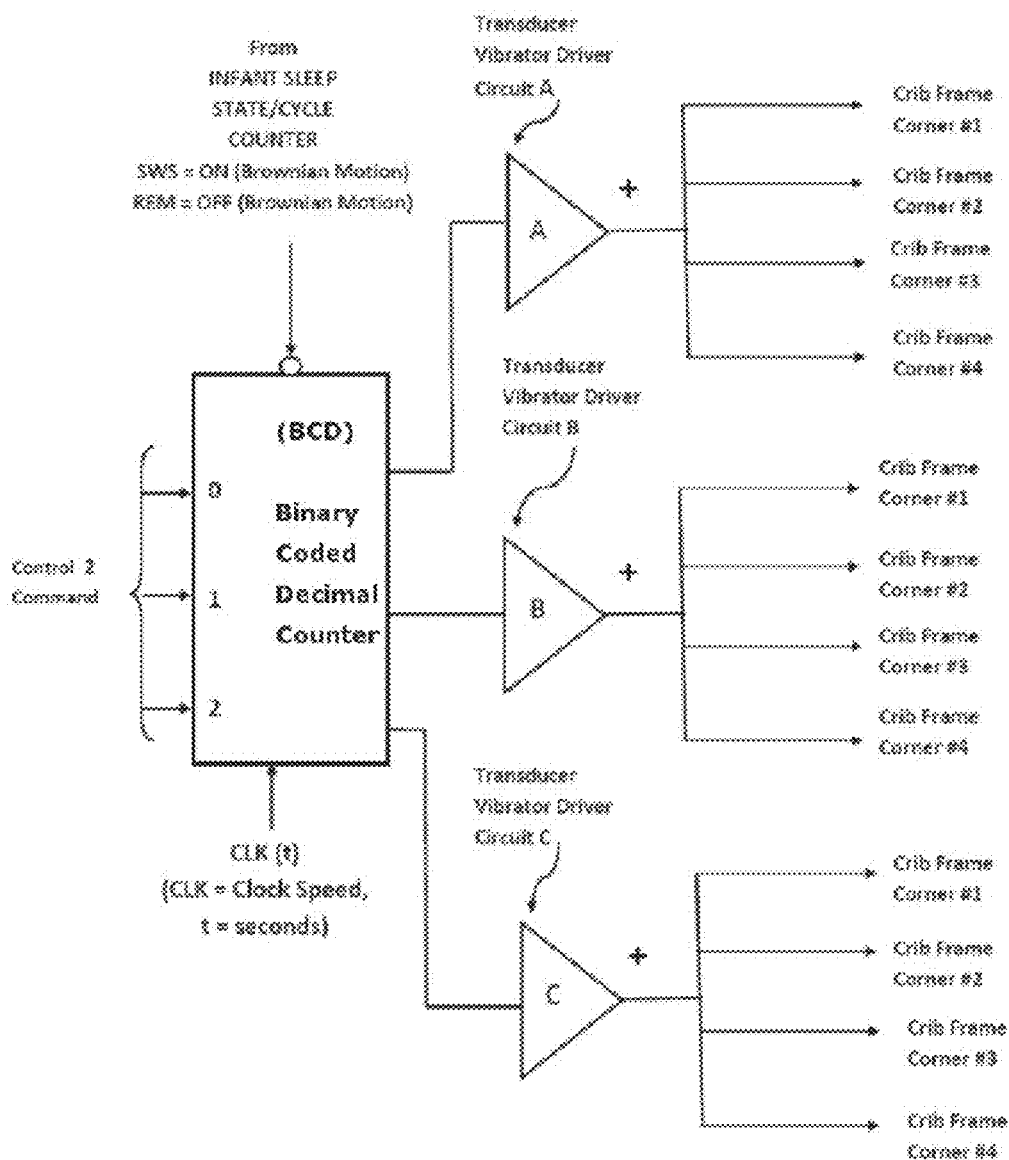
FIG. 20 illustrates a view of the Brownian Motion Circuit. The SRP system applies movement to the infant by moving the crib mattress via the crib frame.

The SRP system embodiments apply movement to the infant by moving the crib mattress via the crib frame. FIG. 20 illustrates the Brownian Motion Circuit. The SRP system applies movement to the infant by moving the crib mattress via the crib frame. FIG. 20 illustrates the Brownian Motion Circuit.

Figures 21, 22:
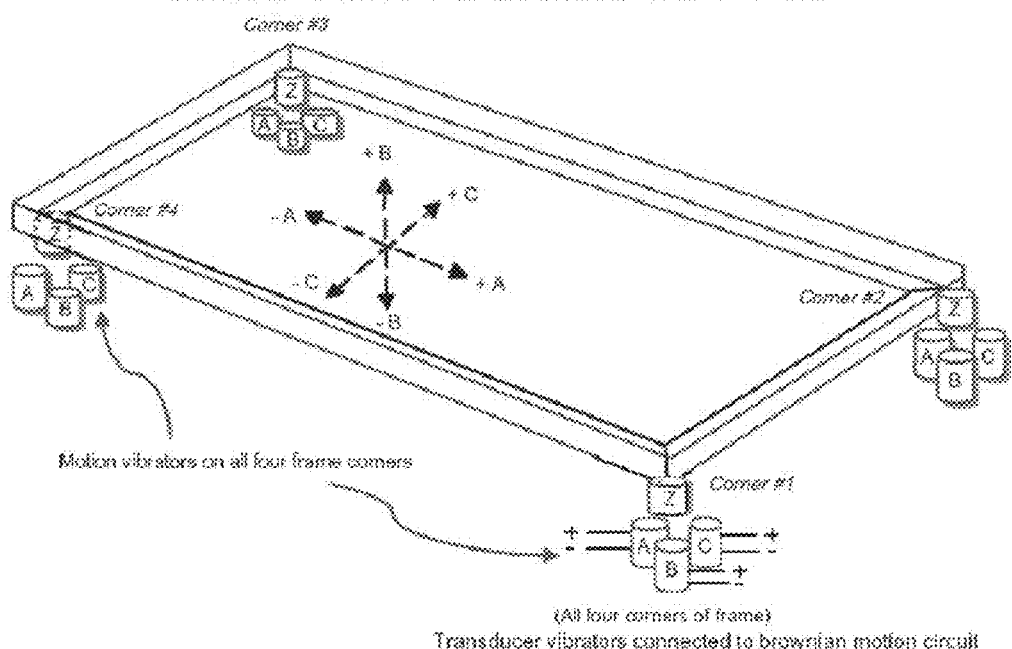
FIG. 21 illustrates a tabular view of Brownian Motion Circuit movement of the infant crib frame via a Brownian Motion Vibrator Activation Matrix.
FIG. 22 illustrates a perspective view of an Infant Mattress Brownian Motion Frame with location of motion vibrators connections and transducer vibrator connections.

Brownian Motion Circuit has three Transducer Vibrator Driver Circuits, "A", "B" and "C". The input to the Transducer Vibrator Driver Circuits is the Binary Coded Decimal (BCD) Counter circuit. Under control of the SRP microcontroller and Control 2 Command, the BCD circuit ensures that only one of the three Transducer Vibrator Driver Circuits is activated at one time. When Transducer Vibrator Driver Circuit "A" is activated, the result is that the set of all four corner transducer vibrators labeled "A" is activated as shown in FIG. 22. This causes the infant crib frame to move as a result of the pull of the "Z" cylinders (which are attached to the crib frame) in the "A" direction by the solenoid effect of the four "A" transducers. FIG. 21 illustrates how the Brownian Motion Circuit moves the infant crib frame via the Brownian Motion Transducer Vibrator Activation Matrix.

When Transducer Vibrator Driver Circuit "B" is activated, the set of the four corner transducer vibrators labeled "B" pull the "Z" cylinders and the crib frame to move in the "B" direction. Likewise, when the Transducer Vibrator Driver Circuit "C" is activated, the set of the four corner transducer vibrators labeled "C" pull the "Z" cylinders and the crib frame to move in the "C" direction.

The frame makes the mattress move in the same direction, which in turn causes the infant to experience a very small movement in the same direction, when the infant is lying down inside the crib mattress.

The ISSCC circuit controls when the Brownian Motion Circuit is activated. The Transducer Vibrators are only active during the time the infant is in the SWS sleep state. The ISSCC turns OFF the Brownian Motion Circuit during the time the infant is in the REM sleep state. The BCD circuit determines the speed of the movement of the infant frame with the Clock (CLK) input and is a function of time (t) in seconds.

The Brownian Motion Circuit indirectly provides movement to the infant's body, which affects the biogenic magnetite nanoparticles in the infant's body through the diffusion coefficient mechanism. This allows better release of ions that induce currents to the dendrites near the nanoparticle, which results in an increased rate of the Inter Spike Interval (ISI) frequencies. The increase in ISI frequencies then provide more neuronal bifurcations which redirects the trajectory of the ensemble of neuronal networks and improves the overall homeostasis of the infant as shown in FIG. 23 (subpanel B). A more stable homeostasis reduces interruptions to the infant's cardiac and respiratory system and reduces the risk of a SIDS related death.

Figure 24:
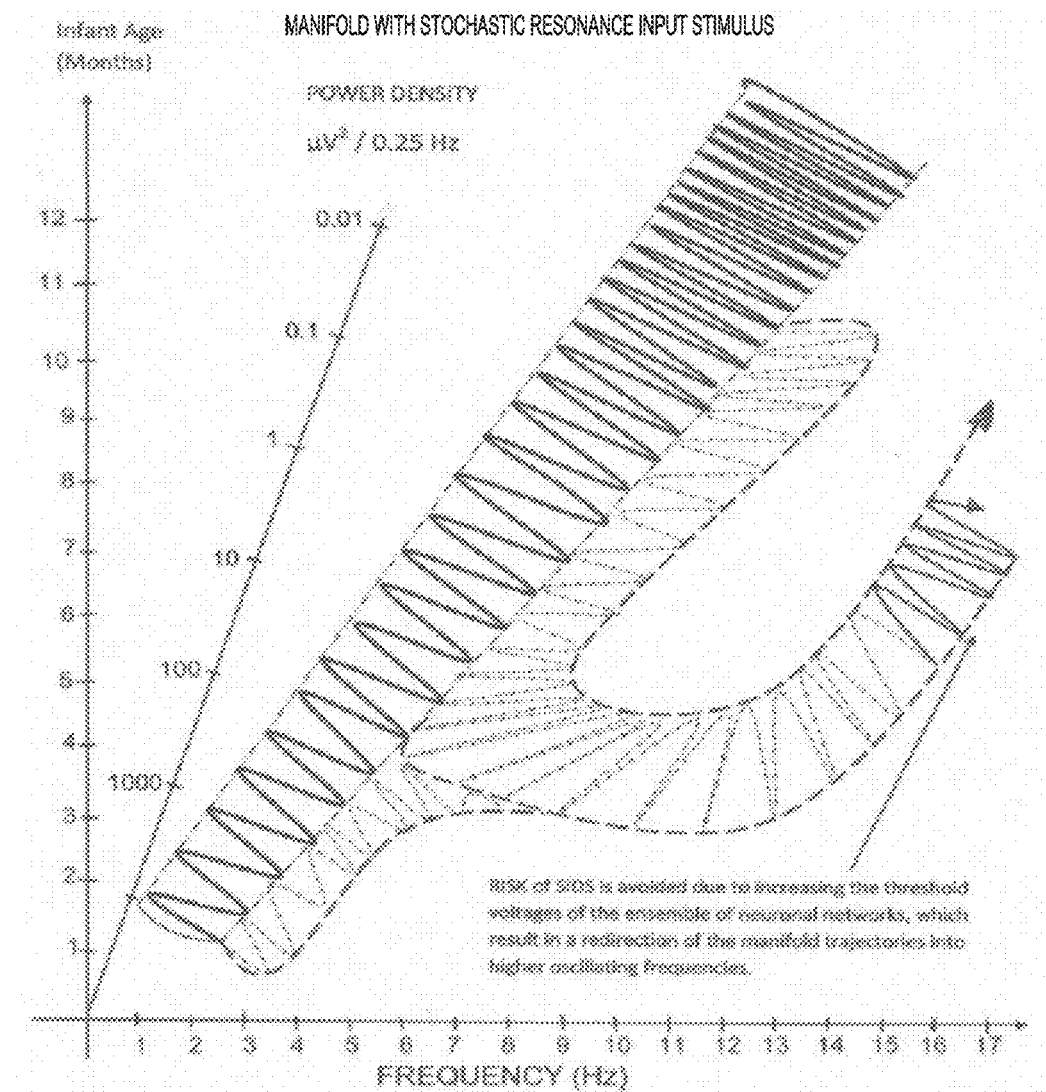
FIG. 24 illustrates an infant neuronal response as a result of the Stochastic Resonance input stimulus from the SRP system.

FIG. 24 illustrates the projected infant neuronal response as a result of the Stochastic Resonance input stimulus from the SRP system. The SRP system should help reduce the risk of SIDS by increasing the threshold voltages of the ensemble of neuronal networks which results in a redirection of the manifold trajectories into higher oscillation frequencies.

In summary the SRP system reduces the number of SIDS related deaths through the application of neurological stimuli to the infant through Stochastic Resonance Noise and Brownian Motion at selected times during sleep. Neurological stimuli are medically known to affect action potentials and to increase the Inter Spike Interval frequency thereby impacting the overall frequency of neural networks oscillations. These higher oscillations would be able to maintain more stable cardiac and respiratory modulations thus preventing incidence of SIDS.

Touchscreen Display

Figure 25:
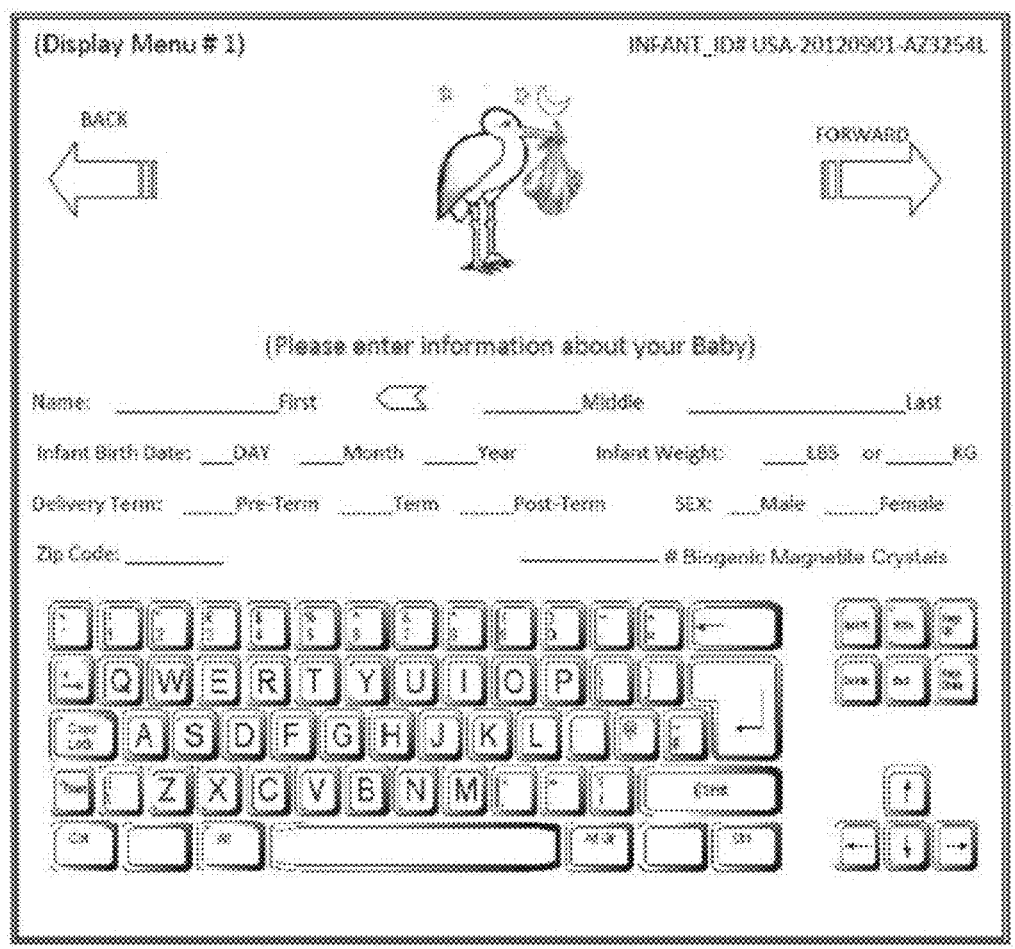
FIG. 25 illustrates Menu 1 input information about infant identification.

The SRP system accepts user information through touch screen display. FIG. 25 illustrates Menu #1, Infant ID Input of the touch screen display. The required information is shown below.

FIG. 26 illustrates Menu #2, Infant's Health Vitals. The SWS and REM sleep states are recorded, along with total sleep time and percentage of SWS and REM sleep cycles.

FIG. 27 illustrates Menu #3, SIDS Survival Matrix. This information is sent to the Crib Display and the remote secure website as well as any web enabled wireless device.

Secure Remote Secure Website and Wireless Mobile Interface

The SRP connects to a remote secure website or wireless mobile device via the interne. The diagram shown in FIG. 28 illustrates the information displayed between the SRP and the remote website and mobile device. Information about Infant's date of birth, age, infant ID#, address, number of biogenic magnetite crystals, delivery term, temperature, cardiac rate, respiratory rate, ISSCC data, Brownian Motion, Stochastic Resonance, white noise level, number & time of REM/SWS cycles, and Rayleigh PDF. A database maintains performance information about the hardware as well as infant statistics.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. A system for preventing Sudden Infant Death Syndrome (SIDS) in an infant, comprising:
    a crib mattress configured to support the infant and including one or more copper noise grids, embedded in the crib mattress, wherein the copper noise grids are configured to provide a neuronal stimulus to the infant in order to prevent SIDS;
    a stimulus circuit configured to generate the neuronal stimulus comprising of time controlled white noise and time controlled cyclic signals, the stimulus circuit configured to adjust the neuronal stimulus based on local white noise power density levels measured at the crib mattress, the stimulus circuit further configured to adjust the neuronal stimulus based on diurnal and seasonal white noise power density level changes; and
    wherein the stimulus circuit further comprises circuitry configured to produce positive and negative adjustable DC voltage levels that are time correlated with epochs of infant sleep states and sleep cycle, the circuitry further configured to adjust the DC voltage levels as a function of the infant's measured levels of biogenic ferromagnetic nanoparticles and crystals and further as a function of infant delivery term, infant's Date of Birth, SIDS probability time line, SIDS Risk Kurtosis Scale and SIDS Survival Matrix, wherein the copper noise grids of the mattress are further configured to receive the neuronal stimulus comprising of the generated white noise and cyclic signals through the circuitry configured to provide the adjustable voltage levels in order to prevent SIDS in the infant.

2. The system of claim 1, further comprising a microcontroller effective for downloading data from a secure website.

3. The system of claim 1, wherein the neuronal stimulus is generated to affect the infant's homeostasis system to establish periodicity of cardiac and respiratory rhythms.

4. The system of claim 3, wherein the neuronal stimulus increases Inter Spike Interval frequencies at selected sleep states and cycles.

5. The system of claim 3, wherein the neuronal stimulus increases neurological bifurcations at selected sleep states and cycles.

6. The system of claim 3, wherein the neuronal stimulus redirects the neurological network ensemble from lower frequency basin attractors to higher frequency basin attractors, at selected sleep states and cycles.

7. The system of claim 1, further comprising a SIDS reduction system with neurological vector phase shifting circuitry to reduce the incidence of SIDS, the reduction system comprising an output of a multitude of variable phase angles, and an output of time correlated drift dependent skewness and kurtosis coefficients.

8. The system of claim 1, wherein the one or more copper noise grids comprises of two copper Stochastic Resonance noise grids.

9. The system of claim 1, further comprising a thermal imaging camera.

10. The system of claim 1, further comprising a Doppler Ultrasound transducer.

* * * * *